(12) United States Patent
Feinberg

(10) Patent No.: US 7,964,342 B2
(45) Date of Patent: Jun. 21, 2011

(54) METHODS FOR ANALYZING METHYLATED CPG ISLANDS AND GC RICH REGIONS

(75) Inventor: Andrew P. Feinberg, Lutherville, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 286 days.

(21) Appl. No.: 10/308,862

(22) Filed: Dec. 2, 2002

(65) Prior Publication Data

US 2003/0232351 A1 Dec. 18, 2003

Related U.S. Application Data

(60) Provisional application No. 60/338,888, filed on Nov. 30, 2001.

(51) Int. Cl.
*C07H 21/04* (2006.01)
*C12Q 1/68* (2006.01)

(52) U.S. Cl. ......... 435/6; 435/91.1; 435/91.2; 536/23.1; 536/24.3

(58) Field of Classification Search ........................ None
See application file for complete search history.

(56) References Cited

U.S. PATENT DOCUMENTS

| | | | |
|---|---|---|---|
| 5,552,277 A | 9/1996 | Nelson et al. | |
| 5,786,146 A | 7/1998 | Herman et al. | |
| 6,235,474 B1 | 5/2001 | Feinberg | 435/6 |
| 6,960,434 B2 * | 11/2005 | Feinberg et al. | 435/6 |

FOREIGN PATENT DOCUMENTS

| | | |
|---|---|---|
| WO | WO 00/18902 A1 | 4/2000 |
| WO | WO 01/90313 A2 | 11/2001 |

OTHER PUBLICATIONS

Esteller et al. (Cancer Research, vol. 58, pp. 4515-4518, Oct. 1998).*
Toyota et al. Cancer Research, vol. 59, pp. 4535-4541, Sep. 1999.*
West, et al., "Hypomethylation of the Amyloid Precursor Protein Gene in the Brain of an Alzheimer's Disease Patient" Journal of Molecular Neuroscience 6 (2):141-146 (1995).*
Widschwendter (Cancer Research, vol. 64, pp. 4472-4480, Jul. 2004).*
Roman-Gomez (Leukemia, vol. 20, pp. 1445-1448, 2006).*
Issa et al. (PNAS, vol. 93, pp. 11757-11762, Oct. 1996).*
Gonzalgo et al. (Cancer Research, vol. 57, pp. 594-599, Feb. 1997).*
Arima, T., et al., "A Novel Imprinted Gene, *HYMAI*, Is Located Within an Imprinted Domain on Human Chromosome 6 Containing *ZAC*," *Genomics*, vol. 67, 2000, pp. 248-255.
Brock, Graham J.R., et al., "Densely Methylated Sequences That are Preferentially Localized at Telomere-Proximal Regions of Human Chromosomes," *Gene*, vol. 240, 1999, pp. 269-277.
Brock, Graham J.R. and Bird, Adrian, "Mosaic Methylation of the Repeat Unit of the Human Ribosomal RNA Genes," *Human Molecular Genetics*, vol. 6, No. 3, 1997, pp. 451-456.

De Smet, Charles, et al., "The Activation of Human Gene *MAGE-1* in Tumor Cells is Correlated with Genome-Wide Demethylation," *Proc. Natl. Acad. Sci*, USA, vol. 93, Jul. 1996, pp. 7149-7153.
Feinberg, Andrew P., "Cancer Epigenetics Takes Center Stage," *PNAS*, vol. 98, No. 2, Jan. 16, 2001, pp. 392-394.
Feinberg, Andrew P., "Methylation Meets Genomics," *Nature Genetics*, vol. 27, Jan. 2001, pp. 9-11.
Strom, Tim M., et al., "Diabetes Insipidus, Diabetes Mellitus, Optic Atrophy and Deafness (DIDMOAD) Caused by Mutations in a Novel Gene (*Wolframin*) Coding for a Predicted Transmembrane Protein,", *Home Molecular Genetics*, vol. 7, No. 13, 1998, pp. 2021-2028.
Bernardi, Giorgio, "The Human Genome: Organization and Evolutionary History," *Annu. Rev. Genetics*, vol. 29, 1995, pp. 445-476.
Choi, Young-Chul, et al. "Molecular Cloning of Mouse Somatic and Testis-Specific H2B Histone Genes Containing a Methylated CpG Island," *DNA and Cell Biology*, vol. 15, No. 6, 1996, pp. 495-504.
Feinberg, Andrew P. and Vogelstein, Bert, "Hypomethylation Distinguishes Genes of Some Human Cancers from their Normal Counterparts," *Letters to Nature*, vol. 301, Jan. 6, 1983, pp. 89-92.
Feinberg, Andrew P., et al., "Reduced Genomic 5-Methylcytosine Content in Human Colonic Neoplasia," *Cancer Research*, vol. 48, Mar. 1, 1988, pp. 1159-1161.
Gonzalgo, Mark L., et al., "Identification and Characterization of Differentially Methylated Regions of Genomic DNA by Methylation-Sensitive Arbitrarily Primed PCR[1]," *Cancer Research*, No. 57, Feb. 15, 1997, pp. 594-599.
Kawai, Jun, et al., "Comparison of DNA Methylation Patterns Among Mouse Cell Lines by Restriction Landmark Genomic Scanning," *Molecular and Cellular Biology*, Nov. 1994, pp. 7421-7427.
Buiting, Karin, et al., "Inherited Microdeletions in the Angelman and Prader-Willi Syndromes Define an Imprinting Centre on Human Chromosome 15," Nature Genetics, vol. 9, Apr. 1995, pp. 395-400.
Serrano, Alfonso, et al., "Methylated CpG Points Identified Within *MAGE-I* Promoter are Involved in Gene Repression," *Int. J. Cancer*, vol. 68, 1996, pp. 464-470.
Singer-Sam, Judith, et al., "A Quantitative HpaII-PCR Assay to Measure Methylation of DNA from a Small Number of Cells," *Nucleic Acids Research*, vol. 18, No. 3, p. 687.
Strichman-Almashanu, L.Z. et al., "A Genome-Wide Screen for Normally Methylated Human CpG Islands That Can Identify Novel Imprinted Genes," *Genome Research*, vol. 12, Mar. 2002, pp. 543-554.
Gloria, et al., "DNA Hypomethylation and Proliferative Activity Are Increased in the Rectal Mucosa of Patients with Long-Standing Ulcerative Colitis", *Am Can. Soc*. 78(11):2300-2306, (1996).
Nambu, et al., "Site-specific Hypomethylation of the c-myc Oncogene in Human Hepatocellular Carcinoma", *Jpn. J. Can. Res*. 78:695-704, (1987).
Aso et al., "Identification and Characterization of Elongin A2, a New Member of the Elongin Family of Transcription Elongation Factors, Specifically Expressed in the Testis", *The Journal of Biological Chemistry*, 275(9):6546-6552 (2000).

(Continued)

*Primary Examiner* — Jeanine A Goldberg
(74) *Attorney, Agent, or Firm* — DLA Piper LLP (US)

(57) ABSTRACT

The present invention provides CpG islands and GC rich regions and methods for identifying methylation states for these CpG islands and GC rich regions. The present invention also provides methods for identifying genes regulated by these CpG islands and GC rich regions, and provides methods for identifying a population of CpG islands and GC rich regions in a genome.

11 Claims, 8 Drawing Sheets

OTHER PUBLICATIONS

Bestor et al., "Epigenetic Effects in Eukaryotic Gene Expression", *Developmental Genetics*, 15:458-462 (1994).

Birren et al., "*Homo sapiens* chromosome 18, clone RP11-49K24, complete sequence", *Database EMBL [Online]*, Nucleotides 122271-123910, Database accession No. AC012254 (Oct. 22, 1999).

Dean C.J., "Preparation and Testing of Monoclonal Antibodies to Recombinant Proteins", *Methods in Molecular Biology, Immunochemical Protocols*, 2nd ed., Humana Press Inc., Totowa, N.J., 80:23-37 (1998).

Gardner et al., "An imprinted locus associated with transient neonatal diabetes mellitus", *Human Molecular Genetics*, 9(4):589-596 (2000).

Giannoukakis et al., "Parental genomic imprinting of the human IGF2 gene", *Nature Genetics*, 4:98-101 (1993).

Mann et al., "Methylated DNA Sequences in Genomic Imprinting", *Critical Reviews in Eukaryotic Gene Expression*, 10(3 & 4):241-257 (2000).

Mitsuya et al., "*LIT1*, an imprinted antisense RNA in the human *KvLQT1* locus identified by screening for differentially expressed transcripts using monochromosomal hybrids", *Human Molecular Genetics*, 8(7):1209-1217 (1999).

Nakagawa et al., "Loss of Imprinting of the Insulin-Like Growth Factor II Gene Occurs by Biallelic Methylation in a Core Region of *H19*-Associated CTCF-Binding Sites in Colorectal Cancer", *PNAS*, 98(2):591-596 (2001).

Onyango et al., "Sequence and Comparative Analysis of the Mouse 1-Megabase Region Orthologous to the Human 11p15 Imprinted Domain", *Genome Research*, Cold Spring Harbor Laboratory Press, 10:1697-1710 (2000).

Sleutels & Barlow, "Investigation of Elements Sufficient to Imprint the Mouse *Air* Promoter", *Molecular and Cellular Biology*, 21(15):5008-5017 (2001).

Steenman et al., "Loss of Imprinting of *IGF2* is Linked to Reduced Expression and Abnormal Methylation of *H19* in Wilms' Tumour", *Nature Genetics*, 7(3):433-439 (1994).

Varrault et al., "Characterization of the Methylation-sensitive Promoter of the Imprinted *ZAC* Gene Supports Its Role in Transient Neonatal Diabetes Mellitus", *The Journal of Biological Chemistry*, 276(22):18653-18656 (2001).

* cited by examiner

```
   1 atggcggcagggtccactacgctgcgcgcagtggggaagctgcag
     M  A  A  G  S  T  T  L  R  A  V  G  K  L  Q
  46 gtgcgtctggccactaagacggagccgaaaaagctagagaaatat
     V  R  L  A  T  K  T  E  P  K  K  L  E  K  Y
  91 ttgcagaaactctccgccttgcccatgaccgcagacatcctggcg
     L  Q  K  L  S  A  L  P  M  T  A  D  I  L  A
 136 gagactggaatcagaaagacggtgaagcgcctgcggaagcaccag
     E  T  G  I  R  K  T  V  K  R  L  R  K  H  Q
 181 cacgtgggcgactttgccagagacttagcggcccggtggaagaag
     H  V  G  D  F  A  R  D  L  A  A  R  W  K  K
 226 ctggtgctcgtggaccgaaacaccgggcctgacccgcaggaccct
     L  V  L  V  D  R  N  T  G  P  D  P  Q  D  P
 271 gaggagagcgcttcccgacagcgcttcggggaggctcttcaggag
     E  E  S  A  S  R  Q  R  F  G  E  A  L  Q  E
 316 cgggaaaaggcctggggcttcccagaaaacgcgacggcccccagg
     R  E  K  A  W  G  F  P  E  N  A  T  A  P  R
 361 agcccatctcacagccctgagcacagacggacagcacgcagaaca
     S  P  S  H  S  P  E  H  R  R  T  A  R  R  T
 406 cctccggggcaacagagacctcacccgaggtctcccagtcgcgag
     P  P  G  Q  Q  R  P  H  P  R  S  P  S  R  E
 451 cccagagccgagagaaagcgccccagaatggccccagctgattcc
     P  R  A  E  R  K  R  P  R  M  A  P  A  D  S
 496 gggccccatcgggaccctccaacgcgcaccgctcccctcccgatg
     G  P  H  R  D  P  P  T  R  T  A  P  L  P  M
 541 cccgagggccctgagcccgctgtgcccggggagcaacccggaaga
     P  E  G  P  E  P  A  V  P  G  E  Q  P  G  R
 586 ggccacgctcacgccgctcagggcgggcctctgctgggtcaaggc
     G  H  A  H  A  A  Q  G  G  P  L  L  G  Q  G
 631 tgccagggccaaccccaggggggaagcggtggggagccacagcaag
     C  Q  G  Q  P  Q  G  E  A  V  G  S  H  S  K
 676 gggcacaaatcgtcccgcggggcttcggctcagaaatcgcctcct
     G  H  K  S  S  R  G  A  S  A  Q  K  S  P  P
 721 gtccaggaaagccagtcagagaggctgcaggcggccggcgctgat
     V  Q  E  S  Q  S  E  R  L  Q  A  A  G  A  D
 766 tccgccgggccgaaaacggtgcccagccatgtcttctcggagctc
     S  A  G  P  K  T  V  P  S  H  V  F  S  E  L
 811 tgggacccctcagaggcctggatgcaggccaactacgatctgctg
     W  D  P  S  E  A  W  M  Q  A  N  Y  D  L  L
 856 tccgcttttgaggccatgacctcccaggcaaacccagaagcactc
     S  A  F  E  A  M  T  S  Q  A  N  P  E  A  L
 901 tccgcgccagcgctccaggaggaagctgcttccctggacgcaga
     S  A  P  A  L  Q  E  E  A  A  F  P  G  R  R
 946 gtgaacgctaagatgccggtgtactcggcctccaggcctgcctgc
     V  N  A  K  M  P  V  Y  S  G  S  R  P  A  C
 991 cagctccaggtgccgacgctgcgccagcagtgcctccgggtgcct
     Q  L  Q  V  P  T  L  R  Q  Q  C  L  R  V  P
1036 aggaacaatccggacgcccctcggcgacgtggaagggtcccctac
     R  N  N  P  D  A  L  G  D  V  E  G  V  P  Y
1081 tcggttcttgaacccgttctggaagggtggacgcccgatcagctg
     S  V  L  E  P  V  L  E  G  W  T  P  D  Q  L
1126 taccgcacagagaaagacaatgccgcactcgctcgagagacagat
     Y  R  T  E  K  D  N  A  A  L  A  R  E  T  D
1171 gaattatggaggattcattgcctccaggacttcaaggaagaaaag
     E  L  W  R  I  H  C  L  Q  D  F  K  E  E  K
1216 ccacaggagcacgagtctcttggcgggagctgtacctgcggcttcgg
     P  Q  E  H  E  S  W  R  E  L  Y  L  R  L  R
1261 gacgcccgagagcagcggctgcgagtagtgaccacgaaaatccga
     D  A  R  E  Q  R  L  R  V  V  T  T  K  I  R
1306 tccgcacgtgaaaacaaacccagcggccgacagacaaagatgatc
     S  A  R  E  N  K  P  S  G  R  Q  T  K  M  I
1351 tgtttcaactctgtggccaagacgccttatgatgcttccaggagg
     C  F  N  S  V  A  K  T  P  Y  D  A  S  R  R
1396 caagagaagtctgcaggagccgctgaccccggaaatggagagatg
     Q  E  K  S  A  G  A  A  D  P  G  N  G  E  M
1441 gagccagccccaagcccgcaggaagcagccaggctccctccggc
     E  P  A  P  K  P  A  G  S  S  Q  A  P  S  G
1486 ctcggggacggcgacggcggcagcgtgagcggcggcggcagcagc
     L  G  D  G  D  G  G  S  V  S  G  G  G  S  S
1531 aaccggcacgcggcgcccgcggacaaaacccgaaaacaggctgcc
     N  R  H  A  A  P  A  D  K  T  R  K  Q  A  A
1576 aagaaagtggccccgctgatggccaaggcaattcgagactacaag
     K  K  V  A  P  L  M  A  K  A  I  R  D  Y  K
1621 ggaagattctcccgacgataa 1884
     G  R  F  S  R  R  *
```

METHODS FOR ANALYZING METHYLATED CPG ISLANDS AND GC RICH REGIONS

RELATED APPLICATION DATA

This application claims the benefit of U.S. Provisional Application Ser. No. 60/338,888 filed Nov. 30, 2001, the entire contents of which is incorporated herein by reference.

STATEMENT OF GOVERNMENT SUPPORT

This invention was made in part with government support under Grant No. CA65145 awarded by the National Institutes of Health. The government may have certain rights in this invention.

BACKGROUND OF THE INVENTION

1. Field of the Invention

The present invention relates generally to methylation of genomic DNA and more specifically to the identification of sequences normally methylated in the genome and their relationship to disease states.

2. Background Information

DNA methylation is central to many mammalian processes including embryonic development, X-inactivation, genomic imprinting, regulation of gene expression, and host defense against parasitic sequences, as well as abnormal processes such as carcinogenesis, fragile site expression, and cytosine to thymine transition mutations. DNA methylation in mammals is achieved by the transfer of a methyl group from S-adenosyl-methionine to the C5 position of cytosine. This reaction is catalyzed by DNA methyltransferases and is specific to cytosines in CpG dinucleotides. Seventy percent of all cytosines in CpG dinucleotides in the human genome are methylated and prone to deamination, resulting in a cytosine to thymine transition. This process leads to an overall reduction in the frequency of guanine and cytosine to about 40% of all nucleotides and a further reduction in the frequency of CpG dinucleotides to about a quarter of their expected frequency (Bird 1986).

The exception to CpG under representation in the genome is CpG islands, which were first identified as Hpa II tiny fragments (Bird et al. 1985), and were later formally defined as sequences >200 bp in length, with a GC content >0.5, and a CpGobs/CpGexp (observed to expected ratio based on GC content) >0.6 (Gardiner-Garden and Frommer 1987). CpG islands have been estimated to constitute 1%-2% of the mammalian genome (Antequera and Bird 1993), and are found in the promoters of all housekeeping genes, as well as in a less conserved position in 40% of genes showing tissue-specific expression (Larsen et al. 1992). The persistence of CpG dinucleotides in CpG islands is largely attributed to a general lack of methylation of CpG islands, regardless of expression status (reviewed in Cross and Bird 1995).

Although CpG islands are believed to be unmethylated, two exceptions to this rule in normal cells are the inactive X chromosome (Yen et al. 1984) and imprinted genes (Ferguson-Smith et al. 1993; Razin and Cedar 1994; Barlow 1995), both of which are associated with methylated CpG islands. Genomic imprinting is the parental origin-specific differential expression of the two alleles of a gene, and most imprinted genes show differential germline methylation of associated CpG islands (reviewed in Ohlsson et al. 2001). A third exception to the rule of methylation exclusion of CpG islands is aberrant methylation of CpG islands in tumors and in immortalized cultured cells, and such CpG island methylation is thought to contribute to carcinogenesis (Herman et al. 1994; Merlo et al. 1995).

Because of the interest in DNA methylation, genomic imprinting, and cancer, several general approaches have been used to identify CpG islands that are differentially methylated in specific cell types, such as screening tumor-normal pairs for cancer-related methylation changes (Huang et al. 1999; Shiraishi et al. 1999; Toyota et al. 1999), or pronuclear transplantation to examine differential parental origin for imprinted genes (Hayashizaki et. 1994; Plass et al. 1996). However, there are no reports of successfully using a systemic effort to identify unique, methylated CpG islands.

There are a variety of genome scanning methods that have been used to identify altered methylation sites in cancer cells. For example, one method involves restriction landmark genomic scanning (Kawai et al., Mol. Cell. Biol. 14:7421-7427, 1994), and another example involves methylation-sensitive arbitrarily primed PCR (Gonzalgo et al., Cancer Res. 57:594-599, 1997). Changes in methylation patterns at specific CpG sites have been monitored by digestion of genomic DNA with methylation-sensitive restriction enzymes followed by Southern analysis of the regions of interest. The digestion-Southern method is a straightforward method but it has inherent disadvantages in that it requires a large amount of DNA (at least or greater than 5 ug) and has a limited scope for analysis of CpG sites (as determined by the presence of recognition sites for methylation-sensitive restriction enzymes). Another method for analyzing changes in methylation patterns involves a PCR-based process that involves digestion of genomic DNA with methylation-sensitive restriction enzymes prior to PCR amplification (Singer-Sam et al., Nucl. Acids Res. 18:687, 1990). However, this method has not been shown effective because of a high degree of false positive signals (methylation present) due to inefficient enzyme digestion of overamplification in a subsequent PCR reaction.

Genomic sequencing has been simplified for analysis of DNA methylation patterns and 5-methylcytosine distribution by using bisulfite treatment (Frommer et al., Proc. Natl. Acad. Sci. USA 89:1827-1831, 1992). Bisulfite treatment of DNA distinguishes methylated from unmethylated cytosines, but original bisulfite genomic sequencing requires large-scale sequencing of multiple plasmid clones to determine overall methylation patterns, which prevents this technique from being commercially useful for determining methylation patterns in any type of a routine diagnostic assay.

In addition, other techniques have been reported which utilize bisulfite treatment of DNA as a starting point for methylation analysis. These include methylation-specific PCR (MSP) (Herman et al. Proc. Natl. Acad. Sci. USA 93:9821-9826, 1992); and restriction enzyme digestion of PCR products amplified from bisulfite-converted DNA (Sadri and Hornsby, Nucl. Acids Res. 24:5058-5059, 1996; and Xiong and Laird, Nucl. Acids. Res. 25:2532-2534, 1997).

PCR techniques have been developed for detection of gene mutations (Kuppuswamy et al., Proc. Natl. Acad. Sci. USA 88:1143-1147, 1991) and quantitation of allelic-specific expression (Szabo and Mann, Genes Dev. 9:3097-3108, 1995; and Singer-Sam et al., PCR Methods Appl. 1:160-163, 1992). Such techniques use internal primers, which anneal to a PCR-generated template and terminate immediately 5' of the single nucleotide to be assayed. However an allelic-specific expression technique has not been tried within the context of assaying for DNA methylation patterns.

Therefore, there remains a need for a method for using a systemic or genome-wide approach to identify unique, methylated CpG islands, GC rich regions and CpG dinucleotides, including normally methylated CpG sequences.

SUMMARY OF THE INVENTION

The present invention is based on the seminal discovery that normally methylated CpG islands or GC rich regions in the genome may lose methylation and this loss of methylation may be used to identify various diseases or disease states in a subject, imprinted genes and other characteristics of the genome.

In another aspect the present invention provides a method for identifying a CpG island or GC rich-regulated gene. It should be understood that while many of the illustrative examples in this invention show CpG islands, the invention includes not only CpG islands, but also GC rich regions and even CpG dinucleotide sequences. Thus, although the term island may be referred to, the term includes other GC rich sequences as well. The method includes identifying a candidate gene located on a chromosome near a CpG island and determining whether the expression of the candidate gene is regulated by methylation of the CpG island or GC rich region. In one illustrative example, the CpG island or GC rich regions used in the method include at least one of SEQ ID NO: 3-31. In certain embodiments, the method includes identifying the methylation state of a CpG island or GC rich region other than SEQ ID NO: 8 (gDMR 3-4), which has been identified as a gDMR (Arima et al. 2000).

In another aspect the present invention provides a method for identifying a population of CpG islands or GC rich regions in a genome. This aspect of the invention utilizes a method for isolating a library of normally methylated CpG island or GC rich regions disclosed herein. A method according to this aspect of the invention provides a genome-wide scan to identify a population of CpG islands or GC rich regions based on the combination of restriction enzymes used for the method. Therefore, a method according to this aspect of the invention identifies multi-copy CpG islands or GC rich regions within repeats as well as single copy CpG islands or GC rich regions. The method includes performing a double digestion by cleaving genomic DNA with both a restriction enzyme that cleaves at a recognition site with an AT content of greater than 50%, preferably greater than 75% AT, most preferably 100% AT, and a restriction endonuclease that cleaves at an unmethylated restriction site comprising greater than 50% CG, preferably greater than 75% GC, most preferably 100% GC, to generate a series of restriction fragments. The series of restriction fragments in length are typically size fractionated as discussed below, and fragments of a specified length (e.g. greater than 500 base pairs) are cloned in a restriction negative bacteria to generate a first library. This first cloning step enriches for CpG islands or GC rich regions and eliminates unmethylated CpG islands or GC rich regions because of the methylcytosine sensitivity of the restriction enzyme that recognizes only unmethylated restriction sites.

In another aspect, the present invention provides an isolated polynucleotide that includes a nucleotide sequence unmethylated in nucleic acid of paternal origin and methylated in nucleic acid of maternal origin. The polynucleotide is about 1638 nucleotides encoding about 546 amino acids and has about 79% amino acid sequence identity to Elongin A2. In one embodiment, the polynucleotide is set forth in SEQ ID NO:1. This polynucleotide appears to be polymorphic at position 910, which can be G or A. In another embodiment, the polynucleotide encodes a polypeptide as set forth in SEQ ID NO:2.

BRIEF DESCRIPTION OF THE DRAWINGS

FIG. 6 shows the nucleotide and amino acid sequence of Elongin A3 (SEQ ID NO: 1 and 2, respectively). The transcription factor SII similarity motif is shown by the boldfaced bases in the top 6 lines of the figure. The nuclear localization signal is shown by the boldfaced bases in the bottom 2 lines of the figure. The site of the (G/A) polymorphism used for imprinting analysis is boldfaced at nucleotide 910, and the PCR primers specific for Elongin A3 are shown in boldfaced type beginning on the lines that have number 811 and 1261 to the left.

DETAILED DESCRIPTION OF THE INVENTION

Figure 1:
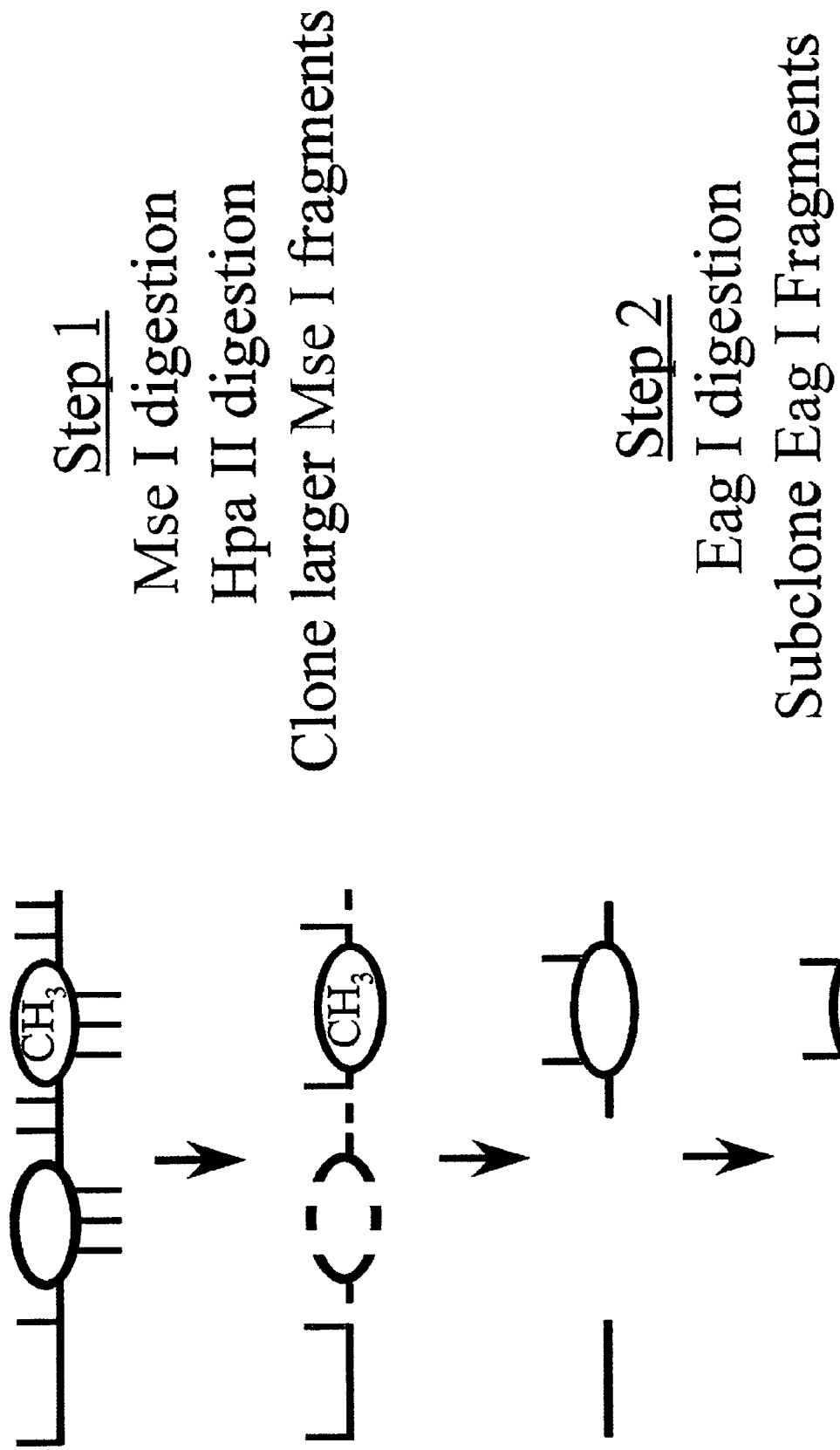
FIG. 1 illustrates an overall strategy for cloning methylated CpG islands. In step 1, genomic DNA is digested with Mse I which cuts between CpG islands, and Hpa II, which cuts unmethylated CpG islands. Mse I fragments containing methylated CpG islands then are transformed into a bacterial strain that does not cut methylated DNA. However, brief bacterial passage leads to loss of methylation of these previously methylated sequences. In step 2, the library DNA is pooled and digested with Eag I, which cuts relatively large fragments within CpG islands, and these fragments are then subcloned.

To identify chromosomal regions that might harbor imprinted genes, the present invention provides a method for generating a library of normally methylated GC rich regions (e.g., a CpG island). Most of the nucleic acid sequences containing methylated CpG islands or GC rich regions isolated using the methods of the invention are high copy number dispersed repeats. However, unique clones in the library can be identified and characterized. Some of the unique clones identified herein were differentially methylated in uniparental tissue of germline origin. These clones are referred to herein as germline differentially methylated regions (gDMRs).

Surprisingly, many of the methylated CpG islands or GC rich regions identified in the Examples herein, are methylated in germline tissues of both parental origins, representing a previously uncharacterized class of normally methylated CpG islands or GC rich regions in the genome, and which we term similarly methylated regions (SMRs). These SMRs, in contrast to the gDMRs, are shown herein to be significantly associated with telomeric band locations, suggesting a potential role for SMRs in chromosome organization. Finally, many of the methylated CpG islands or GC rich regions are on average 85% conserved between mouse and human. While many CpG or GC rich regions are CpG islands, the methods of the invention are not limited to CpG islands.

In one embodiment, the invention provides a method for determining a disease state in a subject by determining the DNA methylation status at a cytosine residue of a CpG sequence in a genomic DNA sample from the subject, wherein hypomethylation of a CpG sequence normally methylated in a subject not having the disease state, is indicative of a disease state in the subject. The CpG sequence is typically found within a GC rich region or a CpG island. The invention methods are preferably used when the subject is a human. Although the disease state is often cancer, the invention is not so limited. The disease state includes other diseases such as multiple sclerosis, Alzheimer's disease, Parkinson's disease, depression and other imbalances of mental stability, atherosclerosis, cystic fibrosis, diabetes, obesity, Crohn's disease, and altered circadian rhythmicity, arthritis, inflammatory reactions or disorders, psoriasis and other skin diseases, autoimmune diseases, allergies, hypertension, anxiety disorders, schizophrenia and other psychoses, osteoporosis, muscular dystrophy, amyotrophic lateral sclerosis or circadian rhythm-related conditions.

In another embodiment, the invention provides a method for determining the DNA methylation status at a cytosine residue of a CpG sequence in a genomic DNA sample by performing methylation state analysis of one or more CpG islands or GC rich regions of a genomic DNA sample, thereby determining the DNA methylation status in the genomic DNA sample. One method for performing methylation state analysis is exemplifed in the Examples herein. In one aspect, the one or more CpG islands or GC rich regions include differentially methylated regions (DMRs). In another aspect, the one or more CpG islands and GC rich regions include similarly methylated regions (SMRs).

In one aspect the present invention provides a method for identifying a CpG island or GC rich region methylation state that includes performing methylation state analysis of one or more CpG islands or GC rich regions of a genomic DNA sample, wherein the one or more CpG islands or GC rich regions are at least one of SEQ ID NOs: 1-31, and in certain embodiments, SEQ ID NOs: 3-7 and 9-31.

In one aspect the present invention provides a method for identifying a CpG island or GC rich region methylation state that includes performing methylation state analysis of one or more CpG islands or GC rich regions of a genomic DNA sample. In one aspect, the one or more CpG islands or GC rich regions are at least one of SEQ ID NOs: 1-31, and in certain embodiments, SEQ ID NOs: 3-7 and 9-31 with the proviso that it is not SEQ ID NO: 8. CpG islands or GC rich regions are sequences greater than 200 bp in length, with a GC content >0.5, and a CpGobs/CpGexp (observed to expected ratio based on GC content) >0.6 (Gardiner-Garden and Frommer 1987).

These methods are useful in providing information regarding gene regulation since it is known that methylation of CpG islands or GC rich regions affects gene expression (Ferguson-Smith et al. 1993; Razin and Cedar 1994; Barlow 1995, Ohlsson et al. 2001, Herman et al. 1994; and Merlo et al. 1995). For example, expression of a tumor suppressor gene can be abolished by de novo DNA methylation of a normally unmethylated CpG island or GC rich region (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995). Consistent with the role of the CpG islands or GC rich regions identified herein in gene regulation, most of the methylated CpG islands or GC rich regions disclosed herein are localized within or near the coding sequence of known genes or of anonymous ESTs within the GenBank or Celera databases. The GC rich regions may be in exons, introns or regulatory regions, for example.

In all the methods described herein, the identification of sequences normally methylated and which have lost methylation is used for identifying a disease or disease state. Such disease or disease state includes cancer, multiple sclerosis, Alzheimer's disease, Parkinson's disease, depression and other imbalances of mental stability, atherosclerosis, cystic fibrosis, diabetes, obesity, Crohn's disease, and altered circadian rhythmicity, arthritis, inflammatory reactions or disorders, psoriasis and other skin diseases, autoimmune diseases, allergies, hypertension, anxiety disorders, schizophrenia and other psychoses, osteoporosis, muscular dystrophy, amyotrophic lateral sclerosis and circadian rhythm-related conditions. Preferred subjects for the present methods are mammals such as humans.

The methylation state of CpG refers to whether a particular cytidine residue in a CpG containing dinucleotide contains any degree of methylation. A CpG dinucleotide or a CpG island or GC rich region is characterized as either methylated or non-methylated based on whether any cytidines of the CpG island or GC rich region are methylated. The methylation state of a CpG island or GC rich region may be completely unmethylated, completely methylated, or partially methylated, and the degree of methylation can be quantified as a percent of residues methylated, as well as individually methylated CpG sites identified. In addition, a particular site can be variably methylated in a population of cells, and that degree of methylation can be quantified. Prior to the present invention, it had been thought that CpG dinucleotides or islands or GC rich regions were typically unmethylated, meaning that the degree of methylation would be nearly zero or quite low (such as less than 10%). Thus, a degree of "normal" methylation greater than the nearly zero amount would be referred to as a "normally" methylated CpG dinucleotide.

Methylation state analysis of CpG islands or GC rich regions can be performed by any method known in the art. Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. Examples of methylation sensitive restriction endonucleases which can be used to detect 5'CpG methylation include SmaI, SacII, EagI, MspI, HpaII, BstUI and BssHII, for example.

Genomic sequencing protocols which identify a 5-MeC residue in genomic DNA as a site that is not cleaved by any of the Maxim Gilbert sequencing reactions can also been used. Other techniques utilize bisulfite treatment of DNA as a starting point for methylation analysis. These include methylation-specific PCR (MSP) (Herman et al. Proc. Natl. Acad. Sci. USA 93:9821-9826, 1992); and restriction enzyme digestion of PCR products amplified from bisulfite-converted DNA (Sadri and Hornsby, Nucl. Acids Res. 24:5058-5059, 1996; and Xiong and Laird, Nucl. Acids. Res. 25:2532-2534, 1997). See also U.S. Pat. Nos. 6,262,171 6,200,756 6,017,704 5,786, 146, all incorporated herein by reference.

In certain embodiments of this aspect of the present invention, CpG island or GC rich region methylation state is determined for similarly methylated regions (SMRs). The Examples included herein utilize methods of the present invention to identify numerous human SMRs. SMRs are CpG islands or GC rich regions that are methylated equally in male and female tissue of germline origin. The SMRs can include at least one of SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 16, SEQ ID NO: 21, SEQ ID NO: 22, SEQ ID NO: 23, SEQ ID NO: 26, SEQ ID NO: 29, and SEQ ID NO: 30, as identified in Table 1. Thus, in one aspect, the invention provides a method for determining the methylation status of a population of similarly methylated regions (SMRs) in a subject by performing methylation status analysis of a population of SMRs of genomic DNA from a human sample. In one aspect, the methylation status of SMRs is correlated with a disease state. In one aspect, the population of SMRs comprises at least two SMRs and in one aspect, at least three SMRs.

Figure 5:
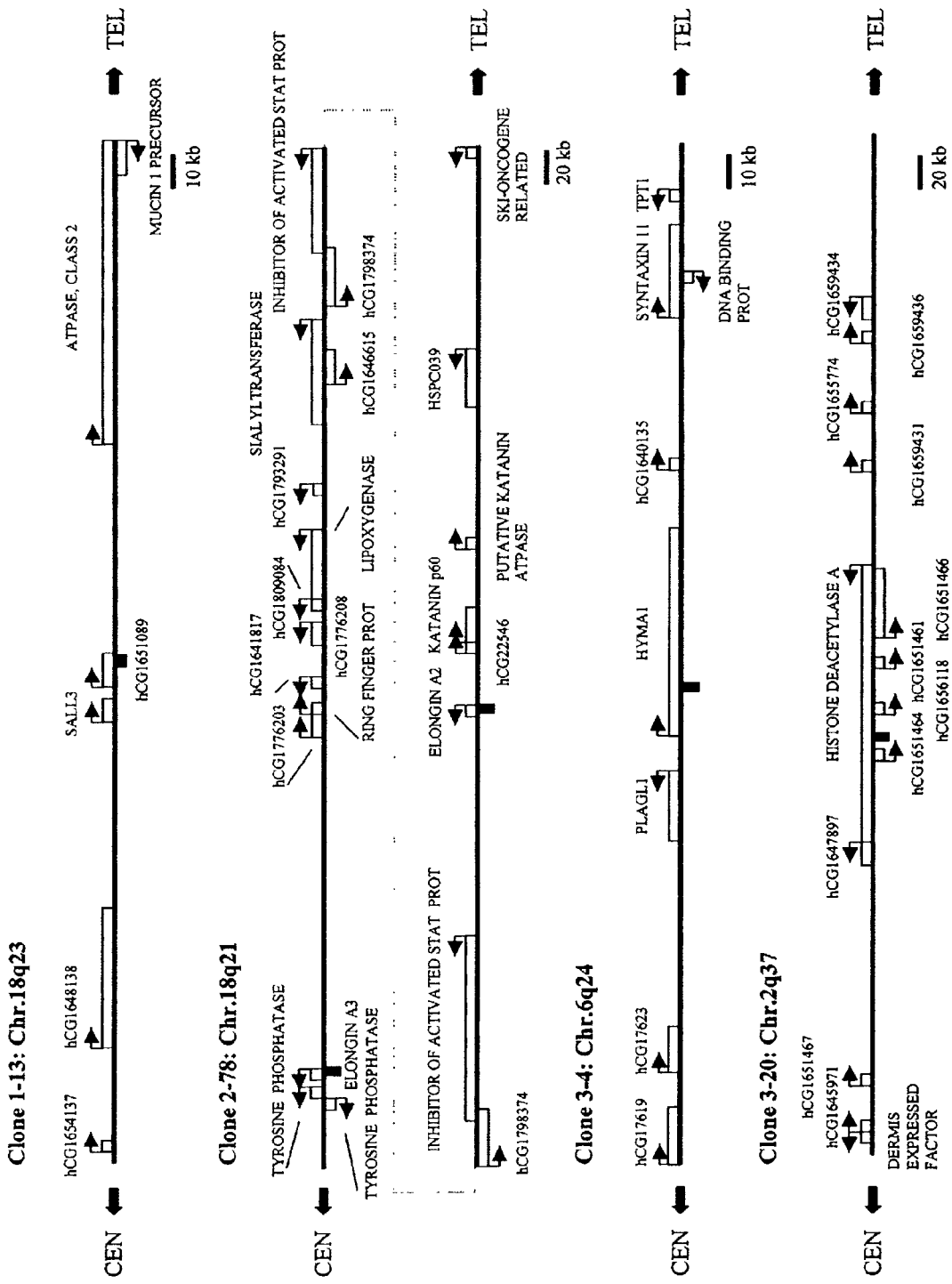
FIG. 5 illustrates the chromosomal location and relationship of representative methylated CpG islands to nearby genes. Genes are indicated with boxes, and the arrows show transcriptional orientation. The methylated CpG islands are shown in shading. In the case of 2-78, the homologous sequence within Elongin A2 is indicated.

Of the sixteen SMRs identified herein, sixteen were localized near the ends of chromosomes, either on the last (n=15) or the penultimate (n=1) subband of the chromosome on which it resides. The method of this aspect of the invention can identify the methylation state of an SMR located near the end of a chromosome. Table 2 and FIG. 5 show the location of specific SMRs of the invention. The Examples included herein also identify CpG islands or GC rich regions that are differentially methylated in germline tissue of male and female origin. These CpGs are referred to herein as germline differentially methylated regions (gDMRs). The method of this aspect of the invention can identify the methylation state of a gDMR. For example, the methylation state can be determined for are least one of SEQ ID NO: 13, SEQ ID NO: 14, SEQ ID NO: 15, SEQ ID NO: 17, SEQ ID NO: 19, SEQ ID NO: 20, SEQ ID NO: 24, SEQ ID NO: 25, SEQ ID NO: 27, SEQ ID NO: 28, and SEQ ID NO: 31.

The methylated CpG islands or GC rich regions identified herein were distributed throughout the genome. There was a striking localization of SMRs near the ends of chromosomes. Sixteen of 17 SMRs were localized near the ends of chromosomes, either on the last (n=15) or the penultimate (n=1) subband of the chromosome on which it resided (Table 2). In contrast, of 12 gDMRs that could be mapped (of the 13 gDMRs studied), only four were localized near the ends of chromosomes (Table 2). This difference was highly statistically significant (P=0.0008, Fisher's exact test). The association of SMRs near the ends of chromosomes is consistent with an observation of densely methylated GC-rich sequences near telomeres, although that study did not describe methylated CpG islands or GC rich regions (Brock et al. 1999). In addition, there was a segregation of gDMRs and SMRs within compartments of differing genomic composition, i.e., isochores, which are regions of several hundred kilobases of relatively homogeneous GC composition (Bernardi 1995). Approximately 75% of the SMRs fell within high isochore regions (G+C 50%), as might be expected from the high GC content of methylated CpG islands or GC rich regions. Surprisingly, however, all of the gDMRs fell within low isochore regions (G+C<50%), i.e., of relatively low GC content, despite the high GC content of the gDMRs themselves (L. Z. Strichman-Almashanu and A. P. Feinberg). This difference was statistically significant (P<0.01, Fisher's exact test). Thus, the gDMRs and SMRs may lie within distinct chromosomal and/or isochore compartments. These results provide the basis for a method to identify epigenetic chromosomal domains. Localization of CpG islands or GC rich regions to the telo/subtelo regions, for example, can be used for identifying imprinted gene domains, disease domains (e.g. p16), chromatin regulated genes controlled at a distance, such as telomerase (TERT) or c-myc by CTCF; and developmentally programmed regions essential for organ formation, such as the brain in Lunyak et al. (Science. Oct. 24, 2002), for example.

The method of this aspect of the invention for identifying the CpG island or GC rich region methylation state can involve identifying the methylation state of one, or more than one CpG island or GC rich region. For example, the methylation state of 2, 3, 4, 5, 6, 7, 8, 9, 10, 11, 12, 13, 14, 15, 20, 25 CpG islands or GC rich regions, or in certain embodiments all 29 CpG islands or GC rich regions disclosed herein (SEQ ID NOs:3-31 is identified). In fact, according to the present invention the methylation state of any of the CpG islands or GC rich regions disclosed in Table 1 can be determined.

In a embodiment of this aspect of the present invention, the methylation state of SEQ ID NO: 27 is identified. gDMR1-13 (SEQ ID NO: 27) is located on 18q23 within a predicted gene of unknown function, and near the SALL3 gene, a candidate gene for 18q deletion syndrome, which involves preferential loss of the paternal allele (Kohlhase et al. 1999).

In another embodiment of this aspect of the present invention, the methylation state of SEQ ID NO: 30 is identified.

SMR1-2 (SEQ ID NO: 30) is located on 19q13.4 within 110 kb of a glioma tumor suppressor candidate gene.

In another embodiment of this aspect of the present invention, the method includes identifying the methylation state of SEQ ID NO: 4 (SMR 3-20). This CpG island or GC rich region is located within the HDAC4 gene (See FIG. 5) and there are several other predicted genes and antisense transcripts near this CpG island or GC rich region.

In another embodiment of this aspect of the present invention, the method includes identifying the methylation state of SEQ ID NO: 26, located within 16 kb from CpG island or GC rich region 2-3.

In another embodiment of this aspect of the present invention, the method includes identifying the methylation state of SEQ ID NO: 21. SEQ ID NO: 21 (SMR 3-110) is located near a predicted apoptosis inhibitor, a septin-like cell division gene, a ras homolog, and a predicted translation initiation factor.

In another embodiment of this aspect of the present invention, the method includes identifying the methylation state of SEQ ID NO: 23. SEQ ID NO: 23 (SMR 1-12) is located near a predicted apoptosis inhibitor, a septin-like cell division gene, a ras homolog, and a predicted translation initiation factor.

In another embodiment of this aspect of the present invention, the method includes identifying the methylation state of SEQ ID NO: 21 (SMR 3-110) and SEQ ID NO: 23 (SMR 1-12). Together these CpGs flank a predicted apoptosis inhibitor, a septin-like cell division gene, a ras homolog, and a predicted translation initiation factor.

In another aspect, the present invention provides a method for determining the methylation state of a series of similarly methylated regions (SMRs) in a subject, the method comprising performing methylation state analysis on a series of SMRs of genomic DNA from a human sample. The present disclosure reveals that the presence of normally-methylated single-copy CpG islands or GC rich regions are more abundant than previously believed. The ability to analyze the methylation state of a series of these normally methylated CpGs provides valuable information regarding the overall methylation state of a genome. This information may provide information regarding overall chromatin state of a genome since SMRs appear to be located near the ends of chromosomes, as illustrated in the Examples herein. Furthermore, such information may provide prognostic, diagnostic, or disease monitoring tools related to cancer, based on previous observations that implicate methylation of genomic methylation in cancer.

The series of SMRs whose methylation state is determined can include at least two, three, four, five, ten, 15, or all of SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO:12, SEQ ID NO: 16, SEQ ID NO: 21, SEQ ID NO: 22, SEQ ID NO: 23, SEQ ID NO: 26, SEQ ID NO: 29, and SEQ ID NO: 30.

As discussed above, methods of the present invention for identifying a CpG island or GC rich region methylation state and methods below for identifying a population of CpG islands or GC rich regions, provide valuable information regarding gene regulation since it is known that methylation of CpG islands or GC rich regions can affect expression of genes located near the CpG island or GC rich region. Accordingly, in one aspect, the present invention provides a method for identifying the presence of an imprinted gene that includes comparing the methylome of genomic DNA of maternal origin with the methylome of genomic DNA of paternal origin, wherein a difference in methylation patterns between the two methylomes is indicative of the presence of an imprinted gene. A methylome is the methylation pattern of an entire genome (Feinberg 2001). DNA methylation serves as an additional layer of genetic information in the genome (Feinberg 2001). Typically, methylation in a genome occurs in CpG islands or GC rich regions. A methylome of a subject can be determined using methods disclosed herein.

The present invention includes an imprinted gene identified by the above method. Genomic imprinting is the parental origin-specific differential expression of the two alleles of a gene. Most imprinted genes show differential germline methylation of associated CpG islands or GC rich regions (reviewed in Ohlsson et al. 2001).

In another embodiment of this aspect of the invention, a method is provided for identifying the presence of an imprinted gene, that includes identifying a population of CpG islands or GC rich regions and identifying a candidate gene found within 200 kilobases of a first CpG island or GC rich region of the population of CpG islands or GC rich regions. A determination is made of whether the candidate gene is regulated by methylation of the first CpG rich region of the population of CpG islands or GC rich regions and preferentially methylated in genomic DNA from paternal or maternal origin. Regulation of the candidate gene by methylation of the first CpG island or GC rich region and paternal or maternal preferential methylation is indicative of an imprinted gene. The present invention includes imprinted genes identified by the above method.

In certain embodiments, the first CpG island or GC rich region is gDMR 3-4 (SEQ ID NO: 27). Interestingly, gDMR 3-4 is located on 18q23, which has been implicated in bipolar affective disorder, specifically harboring a predisposing gene transmitted preferentially through the father (Stine et al. 1995; McMahon et al. 1997). Therefore, the localization of this gDMR herein can serve as a guidepost for identifying candidate imprinted genes for this important disease.

In another aspect the present invention provides a method for identifying a CpG island or GC rich region-regulated gene. The method includes identifying a candidate gene located on a chromosome near a CpG island or GC rich region and determining whether the expression of the candidate gene is regulated by methylation of the CpG island or GC rich region. Preferably, the CpG islands or GC rich regions used in the method include at least one of SEQ ID NO: 3-31. In certain embodiments, the method includes identifying the methylation state of a CpG island or GC rich region other than SEQ ID NO: 8 (gDMR 3-4), which has been identified as a gDMR (Arima et al. 2000).

A CpG island or GC rich region-regulated gene is a gene whose expression is regulated by methylation of a CpG island or GC rich region. A CpG island or GC rich region is located near a candidate gene when it is located within about 2000, 1000, 500, 200 or 100 kilobases of the gene. In other embodiments of the invention, the gene is located within about 50, 25, 10, 5, or 1 kilobase of the gene. In other embodiments, the CpG island or GC rich region is located within a candidate gene. For example, Prader-Willi syndrome CpG island or GC rich region in exon 1 of SNRPN controls expression of genes up to 2 megabases away (See e.g. Buiting et al., Nat Genet., (1995) April; 9(4):395-400).

A determination of genes on the same chromosome as a CpG island or GC rich region, and the approximate distance between a CpG island or GC rich region and a candidate gene can be determined by mapping the CpG island or GC rich region and candidate gene sequences using human genome sequence information on databases such as GenBank (available on the world wide web at ncbi.nlm.nih.gov) or the Celera human gene sequence database.

Methods are known in the art for determining whether expression of a candidate gene is regulated by methylation of a CpG island (see e.g., Ferguson-Smith et al. 1993; Razin and Cedar 1994; Barlow 1995, Ohlsson et al. 2001, Herman et al. 1994; and Merlo et al. 1995). For example, the effect on gene expression of de novo DNA methylation of a normally unmethylated CpG island, can be analyzed (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995).

In one embodiment, the method includes determining whether the candidate gene is regulated by methylation of SEQ ID NO: 13, SEQ ID NO: 14, SEQ ID NO: 15, SEQ ID NO: 17, SEQ ID NO: 19, SEQ ID NO: 20, SEQ ID NO: 24, SEQ ID NO: 25, SEQ ID NO: 27, SEQ ID NO: 28, and SEQ ID NO: 31. This embodiment, includes the CpGs identified herein as being gDMRs.

In a embodiment of this aspect of the present invention, the method includes determining whether the candidate gene is regulated by methylation of SEQ ID NO: 27. gDMR1-13 (SEQ ID NO: 27) is located on 18q23 within a predicted gene of unknown function, and near the SALL3 gene, a candidate gene for 18q deletion syndrome, which involves preferential loss of the paternal allele (Kohlhase et al. 1999).

In another embodiment of this aspect of the present invention, the method includes determining whether the candidate gene is regulated by methylation of SEQ ID NO:30. SMR1-2 (SEQ ID NO: 30) is located on 19q13.4 within 110 kb of a glioma tumor suppressor candidate gene.

In another embodiment of this aspect of the present invention, the method includes determining whether the candidate gene is regulated by methylation of SEQ ID NO: 4 (SMR 3-20). This CpG island or GC rich region is located within the HDAC4 gene (See FIG. 5) and there are several other predicted genes and antisense transcripts near this CpG island or GC rich region.

In another embodiment of this aspect of the present invention, the method includes determining whether the candidate gene is regulated by methylation of SEQ ID NO: 26, located within 16 kb from CpG island or GC rich region 2-3.

In another embodiment of this aspect of the present invention, the method includes determining whether the candidate gene is regulated by methylation of SEQ ID NO:21. SEQ ID NO: 21 (SMR 3-110) is located near a predicted apoptosis inhibitor, a septin-like cell division gene, a ras homolog, and a predicted translation initiation factor.

In another embodiment of this aspect of the present invention, the method includes determining whether the candidate gene is regulated by methylation of SEQ ID NO: 23. SEQ ID NO: 23 (SMR 1-12) is located near a predicted apoptosis inhibitor, a septin-like cell division gene, a ras homolog, and a predicted translation initiation factor.

In another embodiment of this aspect of the present invention, the method includes determining whether the candidate gene is regulated by methylation of SEQ ID NO: 21 (SMR 3-110) and SEQ ID NO: 23 (SMR 1-12). Together these CpGs flank a predicted apoptosis inhibitor, a septin-like cell division gene, a ras homolog, and a predicted translation initiation factor.

In another embodiment of this aspect of the present invention, the method includes determining whether the candidate gene is regulated by methylation of a similarly methylated region (SMR). For example, the method can determine whether the candidate gene is regulated by methylation of SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 16, SEQ ID NO: 21, SEQ ID NO: 22, SEQ ID NO: 23, SEQ ID NO: 26, SEQ ID NO: 29, or SEQ ID NO: 30.

In another aspect the present invention provides a method for identifying a population of CpG islands or GC rich regions in a genome. In one illustrative aspect, the invention utilizes a method for isolating a library of normally methylated CpG islands or GC rich regions disclosed herein. A method according to this aspect of the invention provides a genome-wide scan to identify a population of CpG islands or GC rich regions based on the combination of restriction enzymes used for the method. Therefore, a method according to this aspect of the invention identifies multi-copy CpG islands or GC rich regions within repeats as well as single copy CpG islands or GC rich regions. The method includes performing a double digestion by cleaving genomic DNA with both a restriction enzyme that cleaves at a recognition site with an AT content of greater than 50%, preferably greater than 75% AT, most preferably 100% AT, and a restriction endonuclease that cleaves at an unmethylated restriction site comprising greater than 50% CG, preferably greater than 75% GC, most preferably 100% GC, to generate a series of restriction fragments. The series of restriction fragments in length are typically size fractionated as discussed below, and fragments of a specified length (e.g. greater than 500 base pairs) are cloned in a restriction negative bacteria to generate a first library. This first cloning step enriches for CpG islands or GC rich regions and eliminates unmethylated CpG islands or GC rich regions because of the methylcytosine sensitivity of the restriction enzyme that recognizes only unmethylated restriction sites.

The next step (i.e. the second cloning step) provides further enrichment of CpG islands or GC rich regions by digesting DNA from the first library with an infrequently cutting restriction endonuclease specific for sequences common to GC islands or GC rich regions (e.g., a CpG rich region infrequent restriction endonuclease). An infrequently cutting restriction endonuclease is an endonuclease that recognizes a GC-rich recognition site (e.g., greater than 50% GC content) of at least 6 base pairs in length. (see Gardiner-Garden and Frommer, 1987). As used herein, the methods of the invention include not only CpG islands or GC rich regions (e.g., greater than 200 bp in length and a GC content of >0.5) or GC-islands or GC rich regions in which CpGobs/CpGexp >0.6, but also CpG islands or GC rich regions that do not meet these threshold requirements but which are GC rich and contain multiple CpG dinucleotides. (see also Strichman-Almashanu et al., 2002, herein incorporated by reference in its entirety). Preferably the recognition site recognized by the infrequently cutting restriction endonuclease is has a GC content of at least 75%, most preferably 100% GC. This second cloning step results in isolation of relatively large fragments of CpG islands or GC rich regions that are normally methylated (i.e., survived the first cloning step), but are now unmethylated in the library and therefore amenable to digestion and subcloning.

Virtually any endonuclease that cleaves at a restriction site with a GC content of at least 50%, preferably 75%, and most preferably 100% can be used for the first cloning step in combination with virtually any endonuclease that cleaves at a restriction site with an AT content of at least 50%, preferably 75%, and most preferably 100%. For example, the GC-rich recognition site cleaving enzyme include but are not limited to HpaII, BtgI, SacII, NgoM IV, Bssh II, NaeI, Eag I, BsiE I, Kas I, PspOM I, NarI, SfoI, or Apa I. The AT-rich recognition site cleaving enzyme can be, for example, MseI, SspI, DraI, Tsp509I, ApoI, SspI, AseI, PsiI, DraI. In one embodiment, a double digestion is performed with Mse I, which recognizes the sequence TAAA and Hpa II, which recognizes the sequence CCGG at unmethylated sites.

The CG-rich recognition site cleaving enzyme and the AT-rich recognition site cleaving enzyme can be used in any order or simultaneously depending on the required reaction conditions for the restriction enzymes used, as will be understood.

A restriction negative bacteria is used in the first cloning step in order to avoid bacterial digestion of methylated genomic DNA. Virtually any restriction negative bacteria can be used in the methods of the present invention. For example the restriction negative bacterium can be XL2-Blue MRF'. Many strains of bacteria have been derived that are deficient in, for example, the bacterial enzymes mcrA, mcrCB and mrr. Another example is Strategene XL10 Gold. One bacterium for the first cloning step is the restriction-negative strain XL2-Blue MRF' to avoid bacterial digestion of methylated genomic DNA.

For the restriction digest before the second cloning step, virtually any endonuclease that recognizes a GC-rich recognition site at least 6 base pairs in length can be used. Examples of restriction endonucleases that can be used in this step include Eag 1. In certain embodiments, the restriction endonuclease Eag 1 (recognition sequences CGGCCG) is used. In these embodiments using Eag 1, the resulting library can be referred to as the Eag library.

Preferably, after the digestions before the first and second cloning steps, DNA fragments of specified lengths are isolated and cloned. For example, fragments of at least 100 bp, 250 bp, 500 bp, 2500 bp, and in certain embodiments at least 1000 bp are isolated and cloned. In other embodiments, DNA fragments of specified size ranges can be isolated and cloned. For example, fragments of 100-500 bp, 500-1000 bp, and greater than 1000 bp can be isolated and cloned separately. Methods are well known in the art for size fractionating nucleic acids, such as by using gel purification.

By repeating the aforementioned method for identifying a population of CpG islands or GC rich regions in a genome with different restriction enzymes, and by utilizing various known methods such as methylation specific PCR or bisulfite methods, described herein and known in the art, virtually the entire methylome of an organism can be determined. Alternatively, the method for identifying a population of low copy number CpG islands or GC rich regions can be repeated with different restriction enzymes to identify virtually all the low copy number CpG islands or GC rich regions of a methylome.

The population of CpG islands or GC rich regions in methods of this aspect of the invention can include a subset of least about 50, 100, 200, 250, 500, or 1000 palindromic CpG sites. Additionally, the population of CpG islands or GC rich regions can include at least about 2, 3, 4, 5, 10, 20, 25, 50, or 100 distinct CpG islands or GC rich regions.

The ability to characterize entire methylomes provides further uses for the methods of the invention. For example, methylomes of the same species, for example human methylomes, or portions of a methylome identified using a first set of restriction enzymes to perform the above method of the invention, can be compared to identify methylation differences that are involved in phenotypic differences among individuals of a species. Furthermore, methylomes, or portions thereof, between species can be compared to identify CpG islands or GC rich regions that are important gene expression regulators, by identifying CpG islands or GC rich regions that are conserved between species. The Examples included herein provide a comparison of portions of the methylome of mouse and man to identify conserved CpG islands or GC rich regions.

Furthermore, the method discussed above for identifying a population of CpG islands or GC rich regions in a genome, can be used to identify the methylation state of a series of CpG islands or GC rich regions in various tissues and to determine whether methylation of a CpG island or GC rich region is preferentially related to cells from one parent, or certain tissues, as illustrated in the Examples provided herein. As illustrated in the Examples section hereinbelow, 62 unique CpG island or GC rich region clones were isolated and characterized using methods of the present invention, all of which were methylated and GC-rich, with a GC content >50%. Of these, 43 clones also showed a CpGobs/CpGexp >0.6, of which 30 were studied in detail. These unique methylated CpG islands or GC rich regions mapped to 23 chromosomal regions, and 12 were differentially methylated regions in uniparental tissues of germline origin, i.e., hydatidiform moles (paternal origin) and complete ovarian teratomas (maternal origin), even though many apparently were methylated in somatic tissues. At least two gDMRs mapped near imprinted genes, HYMA1 and a novel homolog of Elongin A and Elongin A2, which we term Elongin A3 (NM_145653), discussed in further detail below. Surprisingly, 18 of the methylated CpG islands or GC rich regions were methylated in germline tissues of both parental origins, representing a previously uncharacterized class of normally methylated CpG islands or GC rich regions in the genome, referred to herein as similarly methylated regions (SMRs). These SMRs, in contrast to the gDMRs, were significantly associated with telomeric band locations (P=0.0008), suggesting a potential role for SMRs in chromosome organization. At least 10 of the methylated CpG islands or GC rich regions identified herein were on average 85% conserved between mouse and human. These sequences will provide a valuable resource in the search for novel imprinted genes, for defining the molecular substrates of the normal methylome, and for identifying novel targets for mammalian chromatin formation.

Evidence for loss of methylation in cancer, (Feinberg and Vogelstein, 1983) has been shown by hypomethylation in genes of some human cancers as compared to their normal counterparts (Nature. Jan. 6, 1983; 301(5895):89-92). More recently, this has been shown in the activation of MAGE melanoma antigen (Serrano, A., Garcia, A., Abril, E., Garrido, F., and Ruiz-Cabello, F. 1996). Methylated CpG points identified within MAGE-1 promoter were shown to be involved in gene repression. (Int. J. Cancer 68: 464-470 and De Smet, C., De Backer, O., Faraoni, I., Lurquin, C., Brasseur, F., and Boon, T. 1996). The activation of human gene MAGE-1 in tumor cells was correlated with genome-wide demethylation (Proc. Natl. Acad. Sci. 93: 7149-7153).

In another aspect the present invention provides a method for identifying a population of low copy number CpG islands or GC rich regions. A method according to this aspect of the invention includes cleaving genomic DNA with both a restriction enzyme that cleaves at a recognition site comprising adenosine and thymidine residues and a restriction endonuclease that cleaves at an unmethylated restriction site comprising cytidine and guanosine residues, to generate a series of restriction fragments and excluding those that are methylated, and cloning restriction fragments of at least 200, 300, 400, 500 and the like kb from the series of restriction fragments in a restriction negative bacteria to generate a first library. This step is similar to the initial double digestion and first cloning step discussed above for the aforementioned aspect of the invention. (See FIG. 1).

After generating the first library, the cloned DNA of the first library is cleaved with a restriction enzyme that cleaves DNA at a restriction site within a CpG island or GC rich region; excluding CpG island or GC rich region fragments that contain repetitive elements while leaving low copy CpG island or GC rich region fragments intact, thereby producing a population of low copy number CpG islands and GC rich region fragments. Such fragments may be at least about 100, 200, 300, 400, 500 and the like kb in size. The method may further include cloning the restriction fragments containing low copy CpG islands and GC rich regions to form a library containing a plurality of low copy CpG island or GC rich region DNA. The "excluding" step is by optionally cleaving cloned DNA of the first library with a restriction enzyme that cleaves DNA at a restriction site within a CpG island or GC rich region repeat sequence or using a methylated CpG binding column, or other methods known to those of skill in the art. A final library containing a plurality of clones is also included in the invention. In one aspect, the GC rich regions are CpG islands.

In another aspect, the present invention provides an isolated polynucleotide that includes a nucleotide sequence unmethylated in nucleic acid of paternal origin and methylated in nucleic acid of maternal origin. The polynucleotide is about 1638 nucleotides encoding about 546 amino acids and has about 79% amino acid sequence identity to Elongin. A2. In embodiment, the polynucleotide is set forth in SEQ ID NO:1. This polynucleotide appears to be polymorphic at position 910, which can be G or A. In another embodiment, the polynucleotide encodes a polypeptide as set forth in SEQ ID NO:2.

Figure 2:
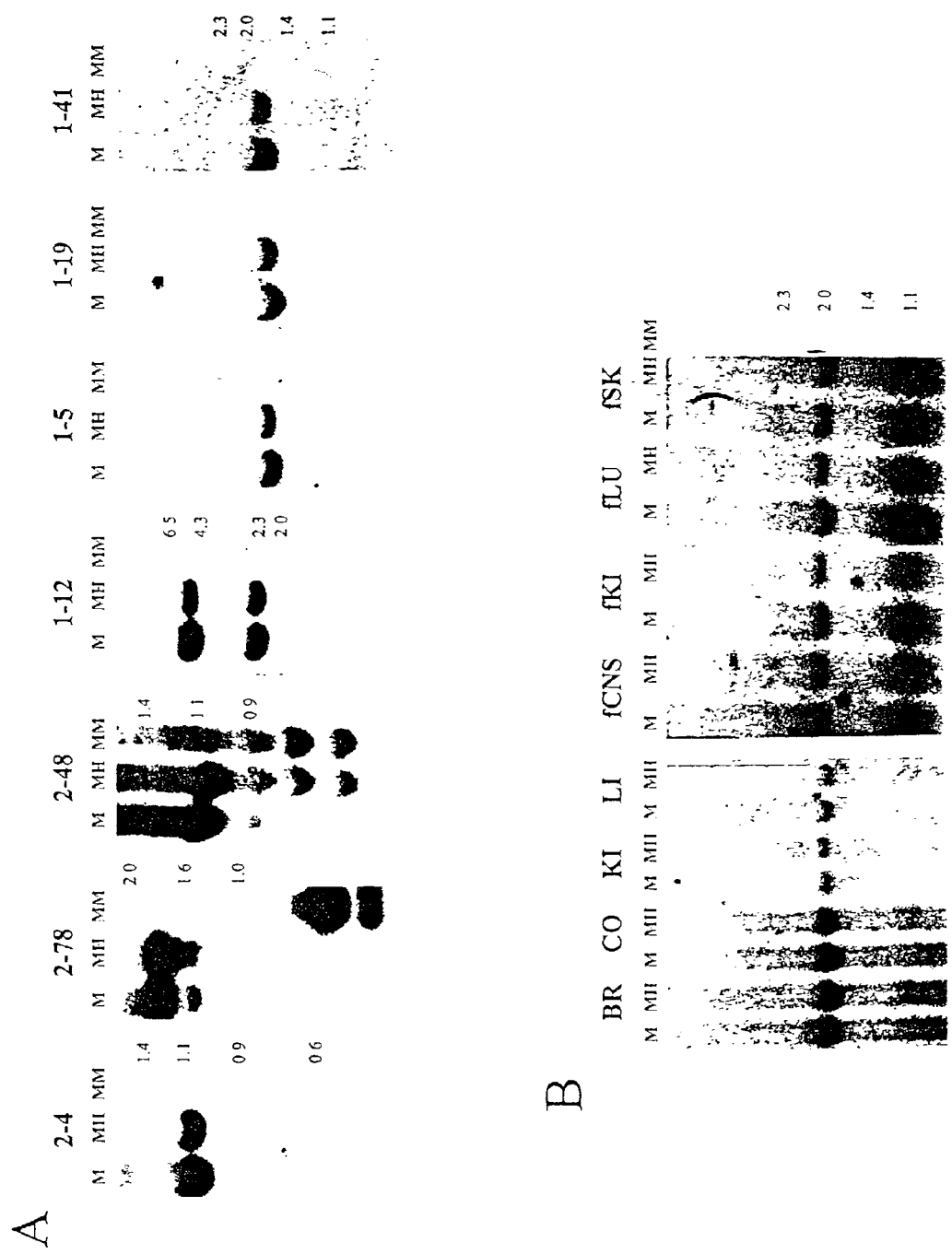
FIGS. 2A and 2B illustrate methylation of CpG islands in normal human DNA. Genomic DNA from peripheral blood lymphocytes (A) or tissues (B) was digested with Mse I (M), Mse I+Hpa II (MH), or Mse I+Msp I (MM). Fragment sizes are indicated to the right. CpG islands used for Southern blot hybridization are indicated in panel A, and CpG island clone 1-19 was used in panel B. Note that there is an Mse I polymorphism in the fetal tissue that is not in the adult tissue, accounting for the presence of two bands in the fetal tissue Mse I digest. Blots were made in duplicate and one set was hybridized to RB to ensure the presence of DNA in the Msp I lane. BR, brain; CO, colon; KI, kidney; LI, liver; fCNS, fetal CNS; fKI, fetal kidney; ELU, fetal lung; fSK, fetal skin.
Figure 3:
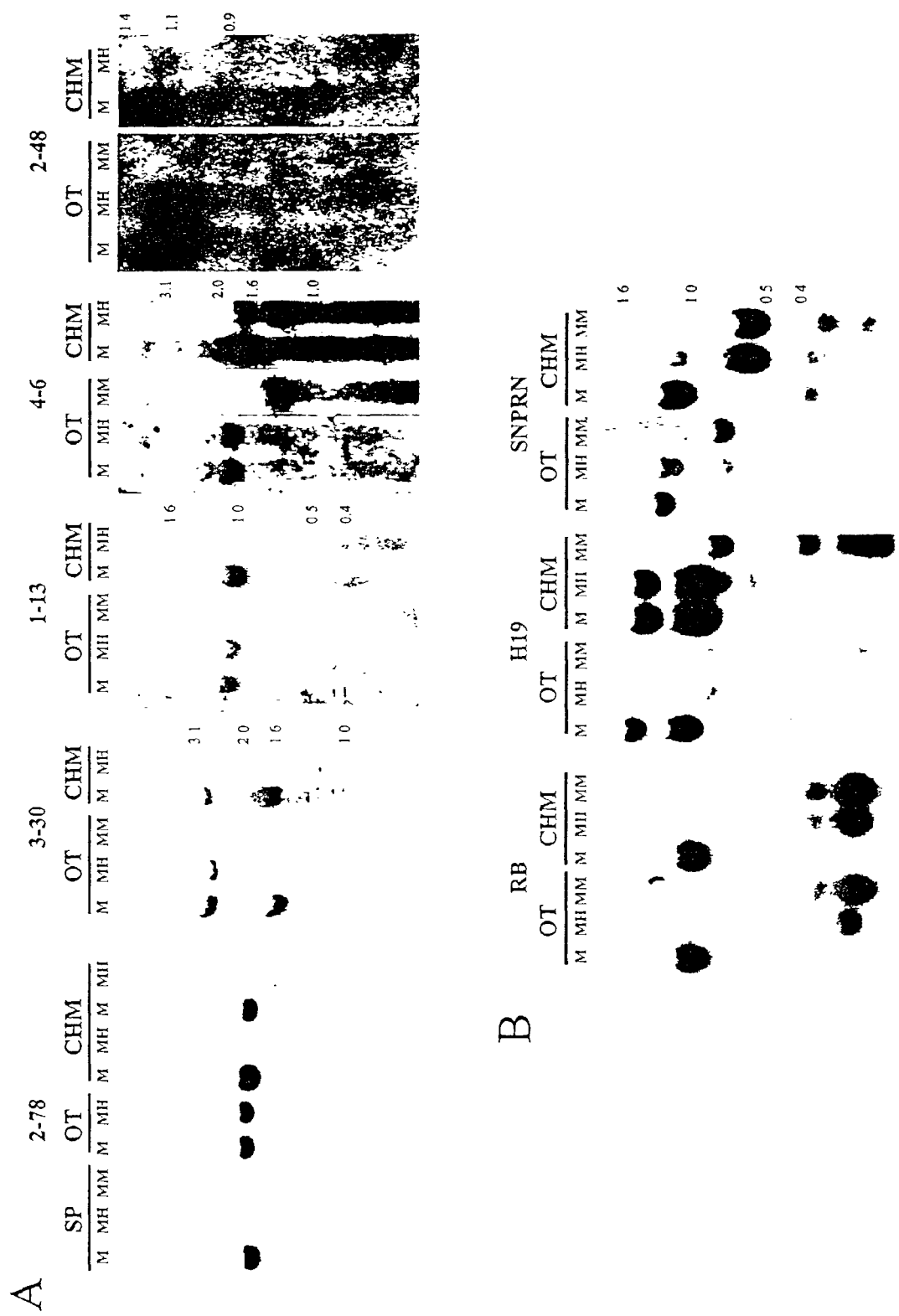
FIGS. 3A and 3B show a series of gels showing differential methylation of novel gDMRs in uniparental tissues of germline origin. Fragment sizes (kb) are indicated to the right. (A) Sperm (SP), ovarian teratoma (OT), or complete hydatidiform mole (CHM) was digested, and Southern blot hybridization was performed with the gDMRs indicated, as described in the legend to FIG. 2. Multiple OT and CHM were examined with similar results, although only one is shown. (B) Similar experiments were performed with an unmethylated CpG island in the retinoblastoma gene (RB), with a CpG island upstream of H19 that shows preferential methylation of the paternal allele, and with a CpG island within the SNRPN gene that shows preferential methylation of the maternal allele.

The polynucleotide of SEQ ID NO: 1 is a novel imprinted gene that was identified using methods of the present invention (as illustrated in the Examples below). The CpG island or GC rich region gDMR 2-78 was localized to 18q21 (FIG. 5) and was completely methylated in all somatic fetal and adult tissues tested (FIG. 2). However, this CpG rich region was unmethylated in CHM and sperm and methylated in OT (FIG. 3A). A BLAST search showed that the CpG island or GC rich region spanned the putative promoter region and body of a gene predicted by GENSCAN (http://genes.mit.edu/GENSCAN), and included 1638 nucleotides encoding 546 amino acids (FIG. 6). BLAST searches of GenBank and Celera databases using the predicted sequences revealed that the predicted gene showed 43% amino acid identity to human transcription elongation factor B (SIII) polypeptide 3 (TCEB3), also known as Elongin A. The novel sequence was even more closely related to a previously identified homolog of Elongin A termed Elongin A2, or TCEB3L, showing 79% amino acid sequence identity to human transcription elongation factor (SIII) Elongin A2 (TCEB3L). We therefore term this gene Elongin A3. An alternative term is TCEB3L2, but for this term to apply, the nomenclature committee will need to rename TCEB3L (Elongin A2) TCEB3L1.

Analysis of allele-specific expression showed monoallelic expression in lung, brain, placenta, and spinal cord, with preferential expression from the maternal allele (FIGS. 7A-D). There was incomplete preferential expression from the maternal allele in two of three kidneys (FIG. 7A, C), and absence of imprint-specific gene expression in one kidney and in the intestine or liver (FIG. 7B, C, D). Thus, Elongin A3 shows tissue-specific imprinting, at least in prenatal development.

In another aspect, the present invention provides an isolated polynucleotide that includes a nucleotide sequence unmethylated in nucleic acid of paternal origin and methylated in nucleic acid of maternal origin. The polynuctiode is about 1638 nucleotides encoding about 546 amino acids and has about 79% amino acid sequence identity to Elongin A2. In a embodiment, the polynucleotide is set forth in SEQ ID NO: 1. This polynucleotide appears to be polymorphic at position 910, which can be G or A. In another embodiment, the polynucleotide encodes a polypeptide as set forth in SEQ ID NO: 2.

The polynucleotide of SEQ ID NO: 1 is a novel imprinted gene that was identified using methods of the present invention (as illustrated in the Examples below). The CpG island or GC rich region gDMR 2-78 was localized to 18q21 (FIG. 5) and was completely methylated in all somatic fetal and adult tissues tested (FIG. 2). However, this CpG island or GC rich region was unmethylated in complete hydatidiform moles (CHM) and sperm and methylated in ovarian teratomas (OT) (FIG. 3A). A BLAST search showed that the CpG island or GC rich region spanned the putative promoter region and body of a gene predicted by GENSCAN (http://genes.mit.edu/GENSCAN), and included 1638 nucleotides encoding 546 amino acids (FIG. 6). BLAST searches of GenBank and Celera databases using the predicted sequences revealed that the predicted gene showed 43% amino acid identity to human transcription elongation factor B (SIII) polypeptide 3 (TCEB3), also known as Elongin A. The novel sequence was even more closely related to a previously identified homolog of Elongin A termed Elongin A2, or TCEB3L, showing 79% amino acid sequence identity to human transcription elongation factor (SIII) Elongin A2 (TCEB3L). We therefore refer to this gene herein as Elongin A3, alternatively TCEB3L2.

The Elongin A3 gene exhibits monoallelic expression in lung, brain, placenta, spinal cord, and some kidneys, with preferential expression from the maternal allele (FIGS. 7A-D). The gene also exhibits an absence of imprint-specific gene expression in one kidney and in the intestine or liver (FIG. 7B, C, D). Thus, Elongin A3 shows tissue-specific imprinting, at least in prenatal development. Based on this expression pattern, the Elongin A3 gene is useful for example, as a marker for tissue-specific imprinting.

It is known from previous studies that the elongin (SIII) complex, which includes elongin A1, strongly stimulates the rate of elongation by RNA polymerase II by suppressing transient pausing by polymerase at many sites along the DNA. Elongin (SIII) is composed of a transcriptionally active A subunit and two small regulatory B and C subunits, which bind stably to each other to form a binary complex that interacts with elongin A and strongly induces its transcriptional activity. Elongin A1, B, and, C are highly conserved between mammals and yeast (Aso, T. et al., Biochem Biophys Res Commun., 241(2):334-40 (1997)).

The elongin (SIII) complex is known to be a potential target for negative regulation by the von Hippel-Lindau (VHL) tumor suppressor protein, which is capable of binding stably to the elongin BC complex and preventing it from activating elongin A. Additionally, it is known that both the elongin A elongation activation domain and the VHL tumor suppressor protein interact with the elongin BC complex through a conserved elongin BC binding site motif that is essential for induction of elongin A activity by elongin BC and for tumor suppression by the VHL protein (Aso T., et al., EMBO J, 15(20):5557-66 (1996)). Elongin A2 is also known to stimulate transcription by RNA Polymerase II.

Based on these results with elongin A1 and elongin A2, elongin A3 polynucleotides and polypeptides of the present invention have utility in vitro transcription reactions, in stimulating transcription by RNA polymerase. Additionally, elongin A3 polynucleotides and polypeptides of the invention have utility in identifying additional tumor suppressor genes which interact with transcriptional machinery since it is known that at least one transcription factor interacts with an elongin complex, as discussed above.

As used herein, the term "isolated," "substantially purified" or "substantially pure" means that the molecule being referred to, for example, a polypeptide or a polynucleotide, is in a form that is relatively free of proteins, nucleic acids, lipids, carbohydrates or other materials with which it is naturally associated. Generally, a substantially pure polypeptide, polynucleotide, or other molecule constitutes at least twenty percent of a sample, generally constitutes at least about fifty percent of a sample, usually constitutes at least about eighty percent of a sample, and particularly constitutes about ninety percent or ninety-five percent or more of a sample. A determination that a polypeptide or a polynucleotide of the invention is substantially pure can be made using well known methods, for example, by performing electrophoresis and identifying the particular molecule as a relatively discrete band. A substantially pure polynucleotide, for example, can be obtained by cloning the polynucleotide, or by chemical or enzymatic synthesis. A substantially pure polypeptide can be obtained, for example, by using methods of protein purification, such as chromatographic or electrophoretic methods.

In another aspect, the present invention provides an isolated polypeptide according to SEQ ID NO:2.

In another aspect, the invention provides, an isolated or purified, polynucleotide that encodes an elongin A3 polypeptide described herein (SEQ ID NO: 2), e.g., a full-length protein or a fragment thereof, e.g., a biologically active portion of the elongin A3 protein. Also included is a nucleic acid fragment suitable for use as a hybridization probe, which can be used, e.g., to identify a nucleic acid molecule encoding a polypeptide of the invention, an elongin A3 mRNA, and fragments suitable for use as primers, e.g., PCR primers for the amplification or mutation of nucleic acid molecules. In one embodiment, an isolated polynucleotide of the invention includes the nucleotide sequence shown in SEQ ID NO: 1, or a portion of any of these nucleotide sequences.

In another embodiment, an isolated polynucleotide of the invention includes a nucleic acid molecule which is a complement of the nucleotide sequence shown in SEQ ID NO: 1, or a portion of any of these nucleotide sequences. In other embodiments, the nucleic acid molecule of the invention is sufficiently complementary to the nucleotide sequence shown in SEQ ID NO: 1, such that it can hybridize (e.g., under high stringency conditions) to the nucleotide sequence shown in SEQ ID NO: 1 or 3, thereby forming a stable duplex.

In one embodiment, an isolated polynucleotide of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: 1, or a portion, preferably of the same length, of any of these nucleotide sequences.

A nucleic acid molecule of the invention can include only a portion of the nucleic acid sequence of SEQ ID NO: 1. For example, such a nucleic acid molecule can include a fragment which can be used as a probe or primer or a fragment encoding a portion of an elongin A3 protein, e.g., an immunogenic or biologically active portion of an elongin A3 protein. The nucleotide sequence determined from the cloning of the elongin A3 gene allows for the generation of probes and primers designed for use in identifying and/or cloning other elongin A3 family members, or fragments thereof, as well as elongin A3 homologues, or fragments thereof, from other species.

In another embodiment, a nucleic acid encodes an polypeptide fragment of elongin A3 described herein. Nucleic acid fragments can encode a specific domain or site described herein or fragments thereof, particularly fragments thereof which are at least 100, 150, 200, 210, 220, 230, 240, 250, 300, 350, 400, 450, 500, 550, or 546 amino acids in length. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, an elongin A3 nucleic acid fragment can include a sequence corresponding to a domain that binds other elongins, similar to the domain of elongin A1 which binds elongins B and C. Elongin A3 probes and primers are provided. Typically a probe/primer is an isolated or purified oligonucleotide. The oligonucleotide typically includes a region of nucleotide sequence that hybridizes under moderate, or preferably high stringency conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO: 1, or of a naturally occurring allelic variant or mutant of SEQ ID NO: 1.

In a embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

In another embodiment a set of primers is provided, e.g., primers suitable for use in a PCR, which can be used to amplify a selected region of a elongin A3 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant.

A nucleic acid fragment can encode an epitope bearing region of a polypeptide described herein. A nucleic acid fragment encoding a "biologically active portion of a elongin A3 polypeptide" can be prepared by isolating a portion of the nucleotide sequence of SEQ ID NO:1, which encodes a polypeptide having a elongin A3 biological activity (e.g., the biological activities of the elongin A3 protein is described herein), expressing the encoded portion of the elongin A3 protein (e.g., by recombinant expression in vitro) and assessing the activity of the encoded portion of the elongin A3 protein. For example, a nucleic acid fragment encoding a biologically active portion of elongin A3 includes a domain that binds with other elongins such as elongin B or elongin C. A nucleic acid fragment encoding a biologically active portion of a elongin A3 polypeptide, can comprise a nucleotide sequence which is greater than 300 or more nucleotides in length.

In certain embodiments, a nucleic acid of the invention includes a nucleotide sequence which is about 300, 400, 500, 600, 700, 800, 900, 1000, 1200, 1400, 1600, 1800, 1900, or more nucleotides in length and hybridizes under moderate or high stringency conditions to a nucleic acid molecule of SEQ ID NO: 1.

In embodiments, the fragment includes at least one, and preferably at least 5, 10, 15, 25, 50, 75, 100, 200, 300, 500, 1000, 1500, or 1620 nucleotides encoding a protein including 5, 10, 15, 20, 25, 30, 40, 50, 100, 200, 210, 220, 230, 240, 250, 300, 350, 400, 450, 500, or 546 consecutive amino acids of SEQ ID NO: 2.

The invention further encompasses nucleic acid molecules that differ from the nucleotide sequence shown in SEQ ID NO: 1. Such differences can be due to degeneracy of the genetic code, and result in a nucleic acid which encodes the same elongin A3 protein as that encoded by the nucleotide sequence disclosed herein. In another embodiment, an isolated polynucleotide of the invention has a nucleotide sequence encoding a protein having an amino acid sequence which differs, by at least 1, but less than 5, 10, 20, 50, or 100 amino acid residues that shown in SEQ ID NO: 2. If alignment is needed for this comparison the sequences should be aligned for maximum homology. "Looped" out sequences from deletions or insertions, or mismatches, are considered differences.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

Nucleic acids of the invention can be chosen for having codons, which are compatible, or noncompatible, for a particular expression system, e.g., the nucleic acid can be one in which at least one codon, or at least 10%, or 20% of the codons has been altered such that the sequence is optimized for expression in E. coli, yeast, human, insect, or CHO cells, for example.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO: 2 or a fragment of this sequence. Such nucleic acid molecules can readily be identified as being able to hybridize under moderate, or preferably high stringency condition, to the nucleotide sequence shown in SEQ ID NO: 2 or a fragment of the sequence. Nucleic acid molecules corresponding to orthologs, homologs, and allelic variants of the elongin A3 cDNAs of the invention can further be isolated by mapping to the same chromosome or locus as the elongin A3 gene.

Allelic variants of elongin A3, e.g., human elongin A3, include both functional and non-functional proteins. Functional allelic variants are naturally occurring amino acid sequence variants of the elongin A3 protein within a population that maintain the ability to increase the speed of transcription by RNA polymerase. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the elongin A3, e.g., human elongin A3, protein within a population that do not have the ability to participate in redox reactions or molecular chaperone interactions. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein. As disclosed herein, a polymorphism identified for elongin A3 includes a G or A residue at position 910.

In another aspect, the invention features, an isolated polynucleotide which is antisense to elongin A3. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire elongin A3 coding strand, or to only a portion thereof.

An antisense nucleic acid can be designed such that it is complementary to the entire coding region of elongin A3 mRNA, but more preferably is an oligonucleotide which is antisense to only a portion of the coding or noncoding region of elongin A3 mRNA. For example, the antisense oligonucleotide can be complementary to the region surrounding the translation start site of elongin A3 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

The invention also provides detectably labeled oligonucleotide primer and probe molecules. Typically, such labels are chemiluminescent, fluorescent, radioactive, or calorimetric. The invention also includes molecular beacon oligonucleotide primer and probe molecules having at least one region which is complementary to a elongin A3 nucleic acid of the invention, two complementary regions one having a fluorophore and one a quencher such that the molecular beacon is useful for quantitating the presence of the elongin A3 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

In another aspect, the invention features, an isolated elongin A3 protein, or fragment, e.g., a biologically active portion, for use as immunogens or antigens to raise or test (or more generally to bind) anti-elongin A3 antibodies. Elongin A3 protein can be isolated from cells or tissue sources using standard protein purification techniques. Elongin A3 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In an embodiment, a elongin A3 polypeptide has a molecular weight, e.g., a deduced molecular weight, preferably ignoring any contribution of post translational modifications, amino acid composition or other physical characteristic of SEQ ID NO: 2 or it has an overall sequence similarity of at least 50%, preferably at least 60%, more preferably at least 70, 80, 90, or 95%, with a polypeptide a of SEQ ID NO: 2.

In another aspect, the invention provides an anti-elongin A3 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The anti-elongin A3 antibody can be a polyclonal or a monoclonal antibody. In other embodiments, the antibody can be recombinantly produced, e.g., produced by phage display or by combinatorial methods.

In embodiments an antibody can be made by immunizing with purified elongin A3 antigen, or a fragment thereof, e.g., a fragment described herein, membrane associated antigen, tissue, e.g., crude tissue preparations, whole cells, preferably living cells, lysed cells, or cell fractions, e.g., membrane fractions. A full-length elongin A3 protein or, antigenic peptide fragment of elongin A3 can be used as an immunogen or can be used to identify anti-elongin A3 antibodies made with other immunogens, e.g., cells, membrane preparations, and the like. The antigenic peptide of elongin A3 should include at least 8 amino acid residues of the amino acid sequence shown in SEQ ID NO: 2 and encompasses an epitope of elongin A3. Preferably, the antigenic peptide includes at least 10 amino acid residues, more preferably at least 15 amino acid residues, even more preferably at least 20 amino acid residues, and most preferably at least 30 amino acid residues.

An anti-elongin A3 antibody (e.g., monoclonal antibody) can be used to isolate elongin A3 by standard techniques, such as affinity chromatography or immunoprecipitation. Moreover, an anti-elongin A3 antibody can be used to detect elongin A3 protein (e.g., in a cellular lysate or cell supernatant) in order to evaluate the abundance and pattern of expression of the protein. Anti-elongin A3 antibodies can be used diagnostically to monitor protein levels in tissue as part of a clinical testing procedure, e.g., to determine the efficacy of a given treatment regimen.

The invention also includes cell lines, e.g., hybridomas, which make an anti-elongin A3 antibody, e.g., and antibody described herein, and method of using said cells to make a elongin A3 antibody.

In another aspect, the invention includes, vectors, preferably expression vectors, containing a nucleic acid encoding an elongin A3 polypeptide, preferably the elongin A3 polypeptide of SEQ ID NO: 2. The vector can be capable of autonomous replication or it can integrate into a host DNA. Viral vectors include, e.g., replication defective retroviruses, adenoviruses and adeno-associated viruses.

A vector can include a elongin A3 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., elongin A3 proteins, mutant forms of elongin A3 proteins, fusion proteins, and the like).

The recombinant expression vectors of the invention can be designed for expression of elongin A3 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England iolabs, Beverly, Mass.) and pRIT5 (Pharmacia, Piscataway, N.J.) which fuse glutathione S-transferase (GST), maltose E binding protein, or protein A, respectively, to the target recombinant protein.

The elongin A3 expression vector can be a yeast expression vector, a vector for expression in insect cells, e.g., a baculovirus expression vector or a vector suitable for expression in mammalian cells. When used in mammalian cells, the expression vector's control functions can be provided by viral regulatory elements. For example, commonly used promoters are derived from polyoma, Adenovirus 2, cytomegalovirus and Simian Virus 40.

Another aspect the invention provides a host cell which includes a nucleic acid molecule described herein, e.g., a elongin A3 nucleic acid molecule within a recombinant expression vector or a elongin A3 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a elongin A3 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell* 23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) an elongin A3 protein. Accordingly, the invention further provides methods for producing an elongin A3 protein using the host cells of the invention. In one embodiment, the method includes culturing the host cell of the invention (into which a recombinant expression vector encoding a elongin A3 protein has been introduced) in a suitable medium such that an elongin A3 protein is produced. In another embodiment, the method further includes isolating an elongin A3 protein from the medium or the host cell.

In another aspect, the invention features, a cell or purified preparation of cells which include a elongin A3 transgene, or which otherwise misexpress elongin A3. The cell preparation can consist of human or non-human cells, e.g., rodent cells, e.g., mouse or rat cells, rabbit cells, or pig cells. In embodiments, the cell or cells include a elongin A3 transgene, e.g., a heterologous form of a elongin A3, e.g., a gene derived from humans (in the case of a non-human cell).

The invention provides non-human transgenic animals. Such animals are useful for studying the function and/or activity of a elongin A3 protein and for identifying and/or evaluating modulators of elongin A3 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous elongin A3 gene has been altered by, e.g., by homologous recombination between the endogenous gene and an exogenous DNA molecule introduced into a cell of the animal, e.g., an embryonic cell of the animal, prior to development of the animal.

Elongin A3 proteins or polypeptides can be expressed in transgenic animals or plants, e.g., a nucleic acid encoding the protein or polypeptide can be introduced into the genome of an animal. In embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also provides a method for identifying the DNA methylation status at a cytosine residue of a CpG sequence in a genomic DNA sample from the subject, wherein hypomethylation of CpG sequences compared to a methylated DNA control sample is indicative of a disease present within the subject. In one aspect, the method is characterized in that a set of CpG positions comprises at least 3 CpG positions that are located in the regulatory region of the same gene. In another aspect, the method is characterized in that the methylation state of at least 3 different sets of CpG positions is identified.

The following examples are intended to illustrate but not limit the invention.

Example 1

Isolation of Normally Methylated CpG Islands or GC Rich Regions from a Genome-Wide Screen This example illustrates a method for isolating normally methylated CpG islands or GC rich regions in a genome-wide screen.

Isolation and Identification of Methylated CpG Islands or GC Rich Regions from Genomic DNA A two-step cloning procedure was used for isolating and identifying methylated CpG islands or GC rich regions from genomic DNA. In the first step, 200 µg of genomic DNA were digested overnight with 1000 units of Hpa II (LTI) followed by a 5-h digest with 600 units of Mse I (NEB), according to the manufacturer's conditions, and the volume was reduced using a SpeedVac concentrator (Savant). Fragments 1 kb were size selected using a Chromaspin+TE, 400 column (Clontech), and fragments between 1-9 kb were purified from a 0.8% gel by electroelution and an Elutip-D column (S&S). The eluate was ethanol precipitated, cloned into the compatible Nde I site of pGEM-4Z, which was first modified to abolish the Sma I site, transformed into the competent cells of the restriction-deficient strain XL2-Blue MRF (Stratagene), and plated onto LB-ampicillin agar plates. Library DNA was prepared directly from plates using a plasmid Maxi kit (Qiagen). In the second step, 100 µg of the Mse I library DNA were digested with 1,000 U of Eag I (NEB) according to the manufacturer's conditions. The digest was ethanol precipitated, and 100-1500-bp fragments were size-selected by purification from a 1.5% agarose gel, cloned into the Eag I site of pBC (Stratagene), and transformed into XL1-Blue MRF' (Stratagene).

DNA Sequencing

DNA sequencing was performed using an ABI 377 automated sequencer following protocols recommended by the manufacturer (Perkin-Elmer). The sequences were analyzed by BLAST search (Altschul et al. 1990) of the GenBank and Celera databases.

Southern Hybridization

Genomic DNA was digested with Mse I alone or Mse I together with a methylcytosine-sensitive (Hpa II, LTI, or Sma I, NEB) or methyl-insensitive (Msp I or Xma I, NEB) restriction endonuclease according to the manufacturer's conditions. Southern hybridization was performed as described (Dyson 1991).

Imprinting Analysis of Elongin A3 Gene

Fetal tissues and matched maternal decidua were obtained from the University of Washington Fetal Tissue Bank. We identified polymorphisms by sequencing fetal and maternal PCR amplified genomic DNA. The following conditions were used for PCR amplifications: 95° C., 2 min; then 40 cycles of 95° C. 1 min, 60° C. 30 sec, 72° C. min; then 72° C. for 9 min. Total RNA was isolated from fetal tissues using RNeasy mini kit (Qiagen). To eliminate DNA contamination from RNA preparations, samples were treated with preamplification-grade DNase I (Invitrogen) according to supplied protocols. RT-PCR was carried out using the Superscript II preamplification system (Invitrogen) and was performed for each sample in the presence and absence (negative controls) of RT. cDNA samples were sequenced only when no bands were obtained with the negative controls. The primers used for the imprinting analysis were EL2AL-1093-1112F: 5'-TCT GCT GTC CGC TTT TGA GG-3' (SEQ ID NO:32) and EL2AL-1526-1550R: 5'-ATC GGA TTT TCG TGG TCA CTA CTC G-3' (SEQ ID NO:33). DNA and cDNA sequencing was run on an ABI-377 automated sequencer following protocols recommended by the manufacturer (Perkin-Elmer).

Isolation of Normally Methylated CpG Islands or GC Rich Regions

A restriction enzyme-based strategy was chosen for isolating methylated CpG islands over a PCR-based strategy, to avoid known problems of amplification bias against GC-rich sequences, and to obtain larger clone inserts than would be possible by a PCR-based approach. DNA from tissue from a male was used, to avoid cloning methylated CpG islands from the inactive X chromosome, and to avoid cell culture-induced DNA methylation. The tissue chosen was a Wilms tumor, because this approach would identify either normally methylated CpG islands or those methylated specifically in this tumor, which is of interest to our laboratory. The plan was to determine after cloning these sequences whether they were methylated in normal cells or in tumors. The first step of the approach (FIG. 1) involved double digestion with Mse I, which recognizes the sequence TTAA and Hpa II, which recognizes the sequence CCGG at unmethylated sites. Mse I digests DNA between CpG islands, and Hpa II digests unmethylated CpG islands into small fragments, as it has a 4-bp recognition sequence. These digestions were followed by gel purification of fragments >1 kb in length. These initial digestions and purification were predicted by computer analysis of GenBank to enrich ~10-fold for CpG islands, and enrichment of known methylated CpG islands (near imprinted genes) was confirmed by Southern blot hybridization. At the same time, this step eliminates all unmethylated CpG islands because of the methylcytosine sensitivity of Hpa II. The restriction fragments obtained by this first step then were cloned into the restriction-negative strain XL2-Blue MRF' to avoid bacterial digestion of methylated genomic DNA, and the resulting genomic library was termed the "Mse library." The second cloning step (FIG. 1) involved further enrichment of CpG islands by digesting the purified Mse I library DNA with an infrequently cutting restriction endonucleases (i.e., recognizing 6 bp CG-rich sequences) specific for sequences common to CpG islands, to isolate relatively large fragments of CpG islands that are normally methylated (i.e., survived the first cloning step), but are now unmethylated in the Mse library and therefore amenable to digestion and subcloning. Most of the work described here was performed by using Eag I (recognition sequence CGGCCG) in this second step, and subcloning Eag I fragments in three size classes separated by agarose gel electrophoresis (100-500 bp, 500-1000 bp, >1000 bp), and the resulting library was termed the Eag library.

Methylated CpG Islands Within Interspersed Repeats

The primary goal was to identify unique methylated CpG islands throughout the genome. However, it quickly became apparent that most of the clones in the Eag library represented high copy number methylated CpG islands. The majority of these clones were derived from a sequence termed SVA, which constituted 70% of the Eag I library, and was not previously known to be methylated. The little-known SVA retroposon contains a GC-rich VNTR region, which embodies a CpG rich region between an Alu-derived region and an LTR-derived region. Only three such elements had previously been described (Kawajiri et al. 1986; Zhu et al. 1992; Shen 1994), although their methylation has not been characterized. A probe termed SVA-U was designed, which was unique to the SVA and present in all of the SVA elements, to analyze copy number and methylation of this sequence in genomic DNA. The copy number was estimated by quantitative Southern hybridization to be 5000 per haploid genome. The SVA elements were found to be completely methylated in all adult somatic tissues examined, including peripheral blood lymphocytes, kidney, adrenal, liver and lung. A somewhat less abundant high copy repeat, representing an additional 20% of the Eag I library, corresponded to the nontranscribed intergenic spacer of ribosomal DNA, which was a known methylated repetitive sequence (Brock and Bird 1997), suggesting that ribosomal gene methylation may be more extensive than was previously suspected. The focus of the current study was on the unique methylated CpG islands that were identified after excluding these sequences.

Example 2

Methylation Analysis of Novel Single Copy CpG Islands or GC Rich Regions

This example illustrates that the methods of the present invention for identifying and isolating methylated CpG islands or GC rich regions are effective for identifying imprinted genes.

Isolation and identification of methylated CpG islands from genomic DNA was performed as described in Example 1, except that to eliminate methylated CpG islands that corresponded to dispersed repetitive sequences, the Mse I library was derived by adding restriction enzymes designed to cleave those sequences and render them unclonable. For 28S and ribosomal DNA, we used Asc I. For SVA, we used Dra III+Sal I, followed by either Acc I or TthIII1.

To isolate single-copy clones, we re-derived the Mse library, adding restriction endonucleases designed to cleave repeat sequences described above, rendering them unclonable (see Methods). After eliminating redundant clones, 62 unique clones were characterized. All of the sequences were GC-rich, i.e., with a measured (C+G)/N>50%, and they ranged in GC content from 55 to 79%. Forty-three (69%) of the clones showed an observed to expected CpG ratio >0.6, meeting the formal definitional requirement of a CpG rich region, and they were characterized further. Nevertheless, most of the remaining clones showed an observed to expected CpG ratio >0.5.

As the original source of DNA was a Wilm's tumor, we had no a priori knowledge of the methylation status of these sequences in normal tissue. Surprisingly, all of the sequences were methylated in normal lymphocyte DNA (FIG. 2A).

Methylation was not restricted to lymphocyte DNA, as it also was observed in both adult and fetal tissues, including brain, gut, kidney, liver, lung, and skin (FIG. 2B). Thus, these sequences represented normally methylated CpG islands.

To determine whether the CpG islands were differentially methylated in the maternal and paternal germline, 30 of the clones were individually hybridized to Southern blots of DNA isolated from ovarian teratomas (OT) and complete hydatidiform moles (CHM), which are of uniparental maternal and paternal origin, respectively (CHM DNA was exhausted at that point). Thirteen clones exhibited methylation in the OT but not or significantly less so in the CHM (Table 1). For example, CpG rich region 2-78 showed complete digestion after Hpa II treatment of genomic DNA isolated from sperm and CHM, similar to the pattern after Msp I digestion (FIG. 3A). In contrast, 2-78 showed an identical pattern after Mse I+Hpa II digestion, as after Mse I alone, in OT (FIG. 3A). Similarly, FIG. 3A shows OT-specific methylation of CpG islands 3-30, 1-13, 4-6, and 2-48, with relative lack of methylation in CHM. These sequences therefore represent differentially methylated regions, because of their different pattern of methylation in germline tissues of male (sperm and CHM) and female (OT) origin. Because many of these sequences also are methylated in somatic tissues, we refer to them as gDMR's (germline differentially methylated regions). All of the gDMR sequences were methylated in OT and not CHM. As a negative control, a CpG rich region associated with the RB gene (retinoblastoma) is unmethylated in both CHM and OT. As a positive control, a CpG rich region upstream of the imprinted gene H19 is preferentially methylated in CHM, and a CpG rich region within the imprinted SNRPN gene is methylated in OT (FIG. 3B).

TABLE 1

Methylated CpG Islands Characterized In Detail

| Clone ID | SEQ. ID No. | Methylation pattern | Chromosomal location | Associated genes Accession no. | Predicted function |
|---|---|---|---|---|---|
| 3-10 | 3 | SMR | 1q44 | 14042537[a] | Similar to Zn finger protein |
|  |  |  |  | 14423768 | Olfactory receptor 2T1 |
|  |  |  |  | hCG1644736 | Similar to olfactory receptor 2T1 |
|  |  |  |  | hCG1724357 | Similar to olfactory receptor 2T1 |
| 3-20 | 4 | SMR | 2q36 | 5174481[a] | Histone deacetylase A |
|  |  |  |  | hCG1651464 |  |
|  |  |  |  | hCG1656118 |  |
|  |  |  |  | hCG1651461 |  |
|  |  |  |  | hCG1651466 |  |
| 1-19 | 5 | SMR | 4p16 | 3777583[a] | WFS1 (wolframin) |
| 1-41 | 6 | SMR | 4q35 | hCG1788598[a] | Similar to mouse pair-rule gene ODZ3 |
|  |  |  |  | hCG1793025[a] | Hypothetical protein |
|  |  |  |  | hCG1787540 | Similar to mouse pair-rule gene ODZ3 |
| 4-8 | 7 | SMR | 4q35 | hCG1788598[a] | Adjacent to but distinct from 1-41 |
| 3-4 | 8 | gDMR | 6q24 | hCG1660630[a] | HYMA1 |
| 4-7 | 9 | SMR | 7p22 | 6806913[a] | Centaurin-α |
|  |  |  |  | hCG1747708 |  |
|  |  |  |  | hCG1790856 |  |
|  |  |  |  | hCG1747710 | Cytochrome P450 homolog |
| 1-30 | 10 | SMR | 7q11.1 | hCG1779529[a] | Rab5 exchange factor homolog |
|  |  |  |  | hCG1779527 | Antisense to hCG1779529 |
|  |  |  |  | hCG1789113 | Antisense to hCG1779529 |
|  |  |  |  | 13642872 | 60S ribosomal prot L35 |
|  |  |  |  | 6572672 | Putative transcription factor |
| 1-22 | 11 | SMR | 7q36 | 11386149[a] | Tyrosine phosphatase |
|  |  |  |  | hCG1799787 | BHLF1 protein |
| 3-2 | 12 | SMR | 8p23 | hCG1659058[a] | Proline-rich mucin homolog |
| 2-5 | 13 | gDMR | 8q21.2 | 17451956 | Similar to antigen GOR |
|  |  |  |  | hCG1757665 |  |
| 2-48 | 14 | gDMR | 9p13 | hCG1659616 |  |
| 1-20 | 15 | gDMR | 10q26 | 13325182a |  |
|  |  |  |  | hCG1799063 |  |
| 3-12 | 16 | SMR | 10q26 | 3122245[a] | Inositol triphosphate phosphatase |
|  |  |  |  | hCG1654478 |  |
| 3-30 | 17 | gDMR | 11q25 | 17456499[a] | Hypothetical gene |
|  |  |  |  | hCG37607 |  |
|  |  |  |  | hCG1745526 | Hypothetical protein |
| 1-5 | 18 | SMR | 13q34 | hCG20146[a] |  |
| 1-21 | 19 | gDMR | 14q32 | 8393715 | Heptacellular cancer candidate |
|  |  |  |  | hCG21408 | Similar to Drosophila CLIP-190 |
| 2-42 | 20 | gDMR | 16p13.1 | hCG15669[a] | Ser/Thr protein kinase |
| 3-110 | 21 | SMR | 17q25 | 8400736[a] | βtubulin cofactor D |
|  |  |  |  | 10435982 |  |
| 2-1 | 22 | SMR | 17q25 | 1655842a | Sulfamidase |
|  |  |  |  | 14149793 | Coiled-coil protein |
| 1-12 | 23 | SMR | 17q25 | hCG1806389 |  |
|  |  |  |  | hCG1796817 |  |
| 2-78 | 24 | gDMR | 18q21 | 13645769[a] | Elongin A3 |
| 3-8 | 25 | gDMR | 18q21 | 13645769[a] | Adjacent to but distince from 2-78 |
| 2-3 | 26 | SMR | 18q23 | 6912444 | Voltage-dependent K+ channel |
|  |  |  |  | 1914872 | Choline-binding protein |
|  |  |  |  | 5326898 | RNA Polymerase II CTD phosphatase |

TABLE 1-continued

Methylated CpG Islands Characterized In Detail

| Clone ID | SEQ. ID No. | Methylation pattern | Chromosomal location | Associated genes Accession no. | Predicted function |
|---|---|---|---|---|---|
| 1-13 | 27 | gDMR | 18q23 | hCG1651089[a] | |
| | | | | 6688241 | SALL3 Spalt-like zinc finger protein |
| | | | | hCG20372 | ATPase |
| | | | | 1651088 | Mucin1 precursor |
| 1-6 | 28 | gDMR | 19p13.1 | 14249150[a] | Hypothetical protein |
| 4-3 | 29 | SMR | 19p13.1 | 9665054[a] | Ser/Thr kinase 11 |
| | | | | hCG23965 | Ankyrin repeat protein |
| | | | | 4506715 | Ribosomal protein S28 |
| | | | | hCG1794585 | |
| | | | | 10732648 | Angiopoietin-like protein |
| 1-2 | 30 | SMR | 19q13.4 | 12053197 | Zinc finger protein |
| | | | | 4505329 | NSF attachment protein |
| | | | | 5901994 | Kaptin-actin binding protein |
| | | | | 5689511 | Na/Ca exchanger protein |
| | | | | 7657128 | Glioma tumor suppressor candidate |
| | | | | 7657054 | EH-Domain containing protein |
| | | | | 7657130 | Glioma tumor suppressor candidate |
| 2-4 | 31 | gDMR | 20q12 | 17484155[a] | Nuclear factor of activated T-cells 2 |
| | | | | hCG1800975 | |
| | | | | hCG1653833 | |
| | | | | 13378306 | Brain RPTmam4 isoform |
| | | | | 110743 | Neurofilament triplet H protein |
| | | | | 7799072 | DNA helicase |

Accession numbers correspond to GenBank entries, within 10 kb of the CpG island, unless there is no GenBank entry, in which case correspond to Celera entries. One additional SMR could not be mapped.
[a]CpG island lies within the transcript.

Figure 4:
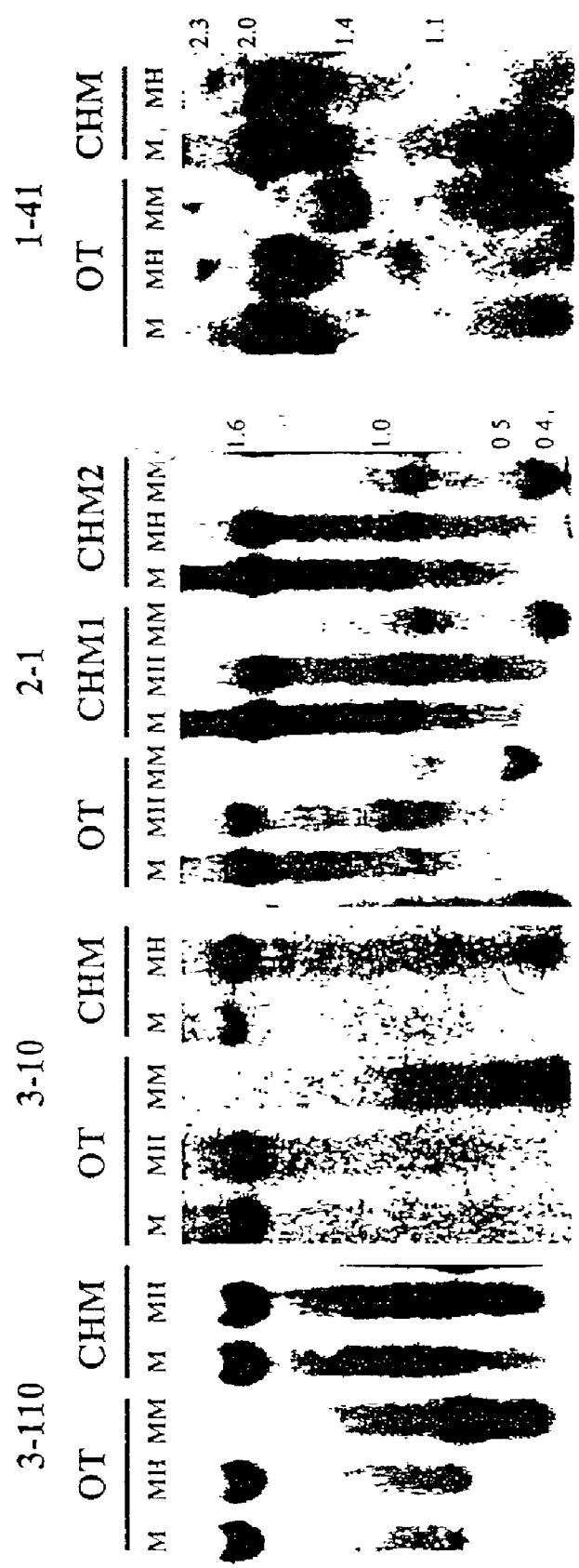
FIG. 4 shows a series of gels showing similar methylation of novel SMRs in uniparental tissues of germline origin. Experiments were performed as described in the legend to FIG. 2, using the SMRs indicated. Fragment sizes are indicated to the right.

An additional 17 clones identified CpG islands that were methylated equally in OT, CHM, and sperm (Table 1). For example, CpG islands 3-110, 3-10, 2-1, and 1-41 showed an identical pattern after Mse I+Hpa II digestion, as after Mse I alone, in OT and CHM (FIG. 4). We termed these sequences SMRs, to connote their comparable methylation in male and female tissue of germline origin. Like the gDMRs, these SMRs were methylated in cells of somatic origin (FIG. 2A).

Example 3

Chromosomal Location of Methylated CPG Rich Regions and Association with Genes This Example shows that many SMRs are located near the ends of chromosomes and identifies CpG islands isolated herein that reside near known genes. Chromosomal locations of the identified CpG islands were determined by identifying corresponding Genbank human genomic DNA sequences of known genomic location, using well-known nucleic acid sequence search tools such as BLAST.

The methylated CpG islands identified here were distributed throughout the genome. There was a striking localization of SMRs near the ends of chromosomes. Sixteen of 17 SMRs were localized near the ends of chromosomes, either on the last (n=15) or the penultimate (n=1) subband of the chromosome on which it resided (Table 2). In contrast, of 12 gDMRs that could be mapped (of the 13 gDMRs studied), only four were localized near the ends of chromosomes (Table 2). This difference was highly statistically significant (P=0.0008, Fisher's exact test). The association of SMRs near the ends of chromosomes is consistent with an observation of densely methylated GC-rich sequences near telomeres, although that study did not describe methylated CpG islands (Brock et al. 1999). In addition, there was a segregation of gDMRs and SMRs within compartments of differing genomic composition, i.e., isochores, which are regions of several hundred kilobases of relatively homogeneous GC composition (Bernardi 1995). Approximately 75% of the SMRs fell within high isochore regions (G+C 50%), as might be expected from the high GC content of methylated CpG islands. Surprisingly, however, all of the gDMRs fell within low isochore regions (G+C<50%), i.e., of relatively low GC content, despite the high GC content of the gDMRs themselves (L. Z. Strichman-Almashanu and A. P. Feinberg). This difference was statistically significant (P<0.01, Fisher's exact test). Thus, the gDMRs and SMRs may lie within distinct chromosomal and/or isochore compartments. These results provide the basis for a method to identify epigenetic chromosomal domains. Localization of CpG islands to the telo/subtelo regions, for example, can be used for identifying imprinted gene domains, disease domains (e.g. p16), chromatin regulated genes controlled at a distance, such as telomerase (TERT) or c-myc by CTCF; and developmentally programmed regions essential for organ formation, such as the brain in Lunyak et al. Science. Oct. 24, 2002 for example.

TABLE 2

Band Location of Methylated CpG Rich regions

| CpG Rich region | Centromeric | Band Location Midchromosome | Telomeric |
|---|---|---|---|
| GDMR | 0 | 8 | 4 |
| SMR | 1 | 0 | 16 |

There were several examples of nonredundant, unique methylated CpG islands localizing to the same chromosomal region. In two cases, two pairs of sequences were adjacent within the genome. Two SMRs on 4q35, 1-41 and 4-8, were adjacent to each other; and two gDMRs on 18q21, 2-78 and 3-8, also were adjacent to each other (Table 1). In addition, 14 methylated CpG islands were located near and on the same chromosomal subband as other methylated CpG islands (Table 1). For example, SMRs 3-110, 2-1, and 1-12 are all on 17q25; two of these sequences, 3-110 and 1-12, lie within 660 kb. In some cases, SMRs and gDMRs were found in relatively close proximity. For example, SMR 2-3 and gDMR 1-13 lie within 1 Mb on 18q23. In addition, gDMR 1-20 and SMR 3-12 are both on 10q26 and separated by ~800 kb (Table 1). All of these data together support the idea that these methylated CpG islands identify specific portions of the genome.

Most of the methylated CpG islands were localized within or near the coding sequence of known genes or of anonymous ESTs within the GenBank or Celera databases. Because of the known ability of DMRs to regulate imprinting over long distances (reviewed in Feinberg 2001), the identity of known or predicted genes within several hundred kilobases of each methylated CpG rich region, was determined. Particularly intriguing was the discovery that gDMR 3-4 was located on 6q24 within HYMA1 (FIG. 5), an imprinted gene involved in diabetes mellitus (Arima et al. 2000). This CpG rich region has been identified independently as a DMR, in a specific analysis of this gene (Arima et al. 2001), and isolation of this sequence using a method of the present invention indicates that these methylated CpG islands may identify imprinted gene domains. gDMR 1-13 was located on 18q23, within a predicted gene of unknown function, and near the SALL3 gene (FIG. 5), which encodes a Spalt-like zinc finger protein that is a candidate gene for 18q deletion syndrome (10610715), which involves preferential loss of the paternal allele (Kohlhase et al. 1999). Interestingly, 18q23 also has been implicated in bipolar affective disorder, specifically harboring a predisposing gene transmitted preferentially through the father (Stine et al. 1995; McMahon et al. 1997). Therefore, the localization of this gDMR may serve as a guidepost for identifying candidate imprinted genes for this important disease. SMR 1-2 was located within 19q 13.4 (FIG. 5). Even though this sequence is an SMR, 19q13.4 contains the imprinted genes PEG3 and ZIM1 (Kim et al. 1999). Given that SMR 1-2 is ~10 Mb from these genes, it is unlikely to lie within the same imprinted gene domain. Nevertheless, it will be of interest to examine nearby genes for their imprinting status, including a glioma tumor suppressor candidate gene located 110 kb telomeric to SMR 1-2. Another interesting gene harboring a methylated CpG rich region was histone deacetylase A (HDAC4), and there were several other predicted genes near this CpG rich region, SMR 3-20 (FIG. 5). In addition, several antisense transcripts are associated with this CpG rich region. Given that HDAC4 is itself involved in chromatin remodeling (Wang et al. 2000), methylation of this region could be involved in a feedback loop controlling chromatin structure. Other genes located near methylated CpG islands included the wolframin gene, a transmembrane protein involved in congenital diabetes (Strom et al. 1998); several olfactory receptor genes; several phosphatase and kinase genes likely involved in signal transduction; several genes for DNA-interacting proteins; and the Peutz-Jeghers syndrome gene STK11 (Table 1). A voltage-dependent potassium channel subunit protein was localized only 16 kb from methylated CpG rich region 2-3 (Table 1), which is of interest given that the voltage-dependent potassium channel KvLQT1 is imprinted (Lee et al. 1997). Finally, in addition to genes directly adjacent to these methylated CpG islands, at least two of the domains flanked by methylated CpG islands harbored several genes within them that may play a role in cancer. For example, contained within the region defined by methylated CpG islands 3-110 and 1-12 are a predicted apoptosis inhibitor, a septin-like cell division gene, a ras homolog, and a predicted translation initiation factor (Table 1).

Example 4

Identification of an Imprinted Gene Homologous to Elongin A

This example illustrates the use of the methods of the present invention for identifying novel genes associated with CpG islands. More specifically, this example illustrates the use of the methods of the present invention to identify the Elongin A gene.

Imprinting Analysis of Elongin A3 Gene

Fetal tissues and matched maternal decidua were obtained from the University of Washington Fetal Tissue Bank. We identified polymorphisms by sequencing fetal and maternal PCR amplified genomic DNA. The following conditions were used for PCR amplifications: 95° C., 2 min; then 40 cycles of 95° C. 1 min, 60° C. 30 sec, 72° C. min; then 72° C. for 9 min. Total RNA was isolated from fetal tissues using RNeasy mini kit (Qiagen). To eliminate DNA contamination from RNA preparations, samples were treated with preamplification-grade DNase I (Invitrogen) according to supplied protocols. RT-PCR was carried out using the Superscript II preamplification system (Invitrogen) and was performed for each sample in the presence and absence (negative controls) of RT. cDNA samples were sequenced only when no bands were obtained with the negative controls. The primers used for the imprinting analysis were EL2AL-1093-1112F: 5'-TCT GCT GTC CGC TTT TGA GG-3' (SEQ ID NO: 32) and EL2AL-1526-1550R: 5'-ATC GGA TTT TCG TGG TCA CTA CTC G-3' (SEQ ID NO: 33). DNA and cDNA sequencing was run on an ABI-377 automated sequencer following protocols recommended by the manufacturer (Perkin-Elmer).

Figure 7:
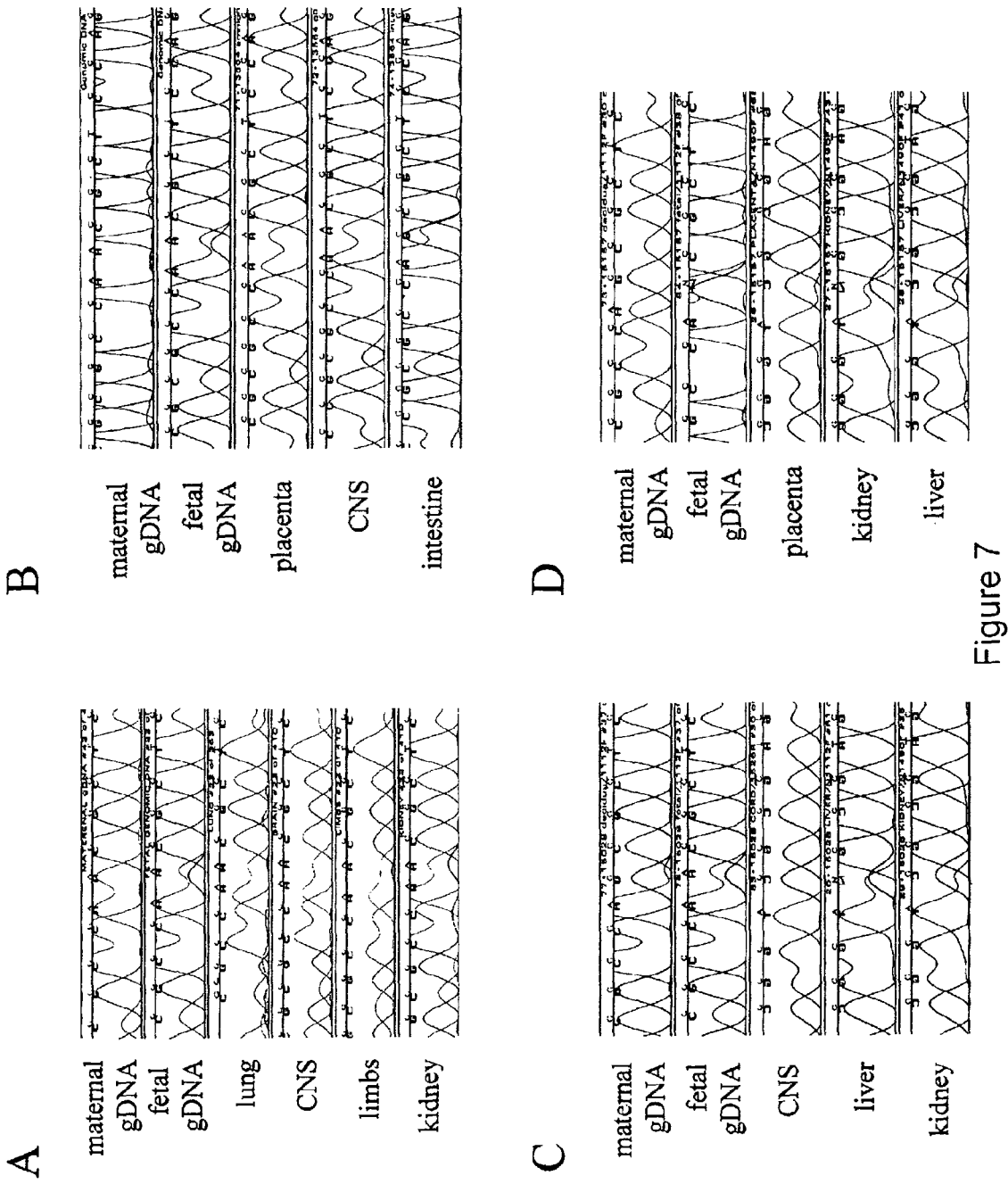
FIGS. 7A-D illustrates tissue-specific imprinting of Elongin A3. The (G/A) polymorphism was used to assess allele-specific expression in four heterozygous fetuses denoted A, B, C, and D. Chromatograms of genomic DNA (gDNA) sequence are included to show heterozygosity, as well as the homozygous maternal decidual DNA indicating parental origin. (A) Monoallelic expression of the maternal allele in lung, central nervous system (CNS), and limbs, and biallelic expression in kidney. (B) Monoallelic expression of the maternal allele in placenta and CNS, and biallelic expression in intestine. (C) Monoallelic expression of the maternal allele in CNS, biallelic expression in kidney and liver. (D) Monoallelic expression of the maternal allele in placenta, and biallelic expression in kidney and liver. Sequencing was done bidirectionally in all cases, and monoallelic expression of the maternal allele did not depend on whether that allele was A or G.

In addition to HYMA1, described above, a DMR within the IGF2R contains an Eag I site, and as predicted, this gene also was found in the Eag library. Allele-specific expression of genes near methylated islands was examined. gDMR 2-78 was localized to 18q21 (FIG. 5) and was completely methylated in all somatic fetal and adult tissues tested (FIG. 2). However, this CpG rich region was unmethylated in CHM and sperm and methylated in OT (FIG. 3A). A BLAST search showed that the CpG rich region spanned the putative promoter region and body of a gene predicted by GENSCAN (http://genes.mit.edu/GENSCAN), and included 1638 nucleotides encoding 546 amino acids (FIG. 6). BLAST searches of GenBank and Celera databases using the predicted sequences revealed that the predicted gene showed 43% amino acid identity to human transcription elongation factor B (SIII) polypeptide 3 (TCEB3), also known as Elongin A. The novel sequence was even more closely related to a previously identified homolog of Elongin A termed Elongin A2, or TCEB3L, showing 79% amino acid sequence identity to human transcription elongation factor (SIII) Elongin A2 (TCEB3L). To determine whether 2-78 represented a genuine transcript, and if so, whether the gene is imprinted, primers were designed that would amplify 2-78 but not Elongin A2, and amplification products were of the expected size. Sequencing demonstrated that the amplified cDNA corresponded to 2-78 and not Elongin A2, based on sequence differences between the two genes within the PCR product. Analyzing DNA samples from fetal tissues, we then identified a polymorphism at nucleotide 910 (G/A) of 2-78. Four fetuses heterozygous for this polymorphism were identified, in which maternal decidua DNA was available and homozygous, allowing the identification of parental origin in the fetal samples (FIG. 7). Reverse transcriptase PCR (RT-PCR) analysis of tissues from these fetuses showed that the gene was indeed transcribed. We therefore term this gene Elongin A3. An alternative term is TCEB3L2, but for this term to apply, the nomenclature committee will need to rename TCEB3L (Elongin A2) TCEB3L1.

Analysis of allele-specific expression showed monoallelic expression of lung, brain, placenta, and spinal cord, with preferential expression from the maternal allele (FIGS. 7A-D). There was incomplete preferential expression from the maternal allele in two of three kidneys (FIG. 7A, C), and absence of imprint-specific gene expression in one kidney and in the intestine or liver (FIG. 7B, C, D). Thus, Elongin A3 shows tissue-specific imprinting, at least in prenatal development. Therefore, the isolation of these novel CpG islands does enable the identification of novel human imprinted genes.

Example 5

Species Conservation of Methylated CpG Rich Regions

This example illustrates that the CpG islands identified herein are conserved among mammalian species and can be used to identify nearby regulatory elements conserved between species.

Figure 8:
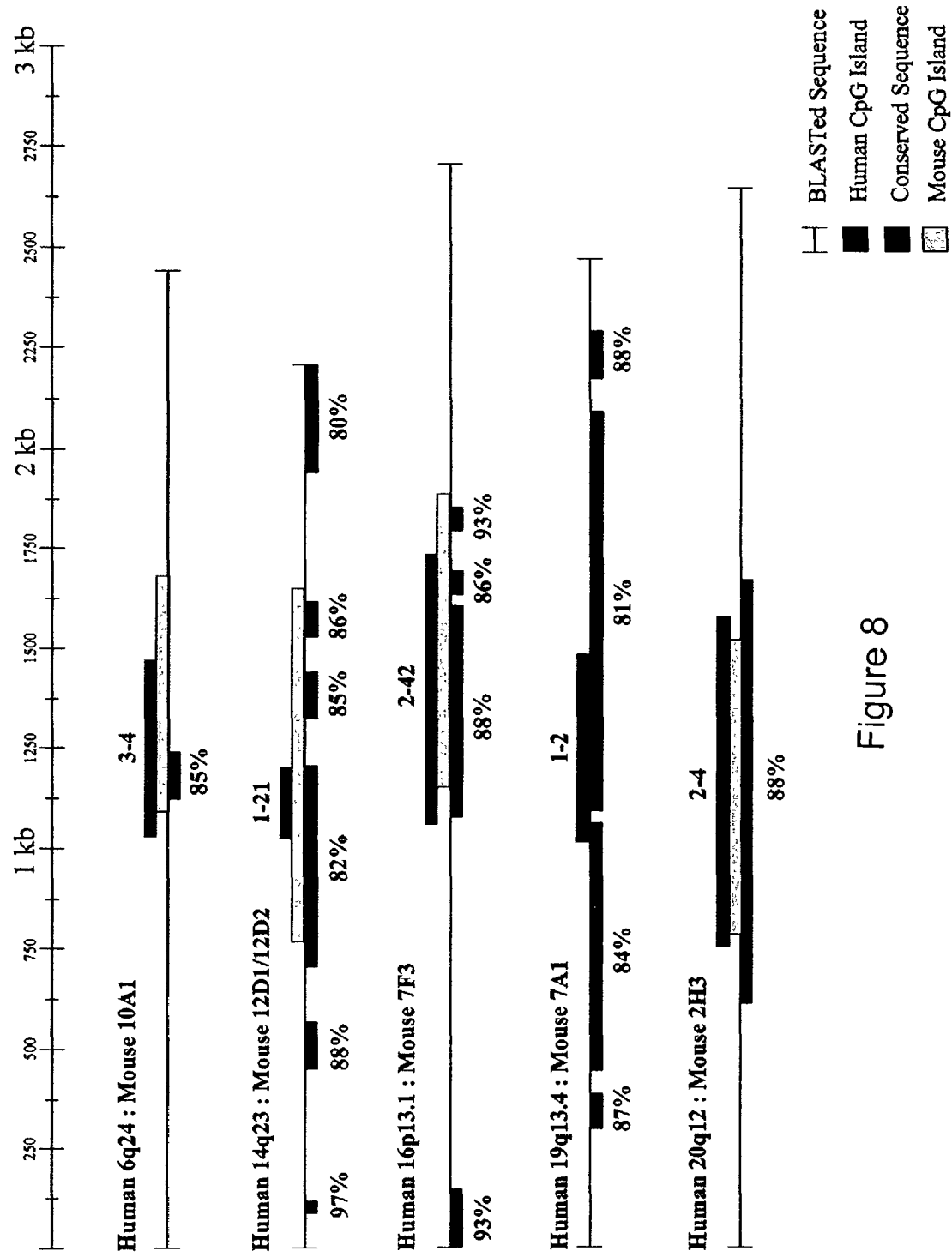
FIG. 8 shows sequence conservation of methylated CpG islands between human and mouse. Human methylated CpG islands and ~1 kb of flanking DNA were compared to mouse sequence, synteny was confirmed, the corresponding mouse CpG islands were identified, and regions of conservation (percentage shown) were determined. In the case of gDMR 1-21, the corresponding mouse sequence, while GC-rich, showed an observed to expected CpG ratio of 0.45-0.50 and therefore was not classified as a CpG island.

As further confirmation of the importance of the methylated CpG islands that were isolated, their sequence conservation in the mouse was ascertained using the Celera mouse genome database. Thirteen (46%) of the 30 human noncontiguous methylated CpG islands matched sequences within the mouse genome at 86.9±4.9% identity (FIG. 8). Furthermore, in some cases, the region of conservation extended beyond the CpG rich region itself. For example, gDMR 1-21 showed, in addition to a 558 bp, 82% conserved region including the CpG rich region, five additional conserved sequences within 1 kb of the CpG rich region. These additional sequences varied from 80-97% identity (FIG. 8). Most of the conserved sequences outside of the CpG islands themselves were not predicted genes, and thus may represent conserved regulatory sequences. In all cases in which BLAST analysis of the CpG rich region and flanking 1 kb on each side was performed, and in which any sequence conservation was found, the CpG rich region itself was conserved, again supporting the idea that these CpG islands play an important role.

Example 6

Normally Methylated CpG Islands and GC Rich Sequences

This Example provides further insight into the methods of the present invention and the conclusions reported herein. A major conclusion of the previous Examples is the identification of a subset of unique CpG islands that are methylated in normal tissues, in the first systematic effort to identify such sequences. The experiments were designed to identify CpG islands that are methylated differentially in germline-derived tissues or differentially in cancers. However, no CpG islands methylated specifically in tumors were found, but slightly more than one half of the unique methylated CpG islands were methylated in germline-derived tissues of both maternal and paternal origin. Conventional wisdom holds that CpG islands are unmethylated, with the exception of the inactive X chromosome, imprinted genes, and tumors. However, rare exceptions to this rule have been described. Some repeated sequences harboring CpG islands have been found to be methylated. Methylation of a mouse testis-specific histone H2B gene has been reported (Choi et al. 1996), and others have found methylation of some ribosomal gene sequences (Brock and Bird 1997). Indeed, methylation of one of these repeat sequences, the rDNA nontranscribed spacer, previously was found after genomic purification from a methyl-CpG binding protein column (Brock and Bird 1997), and the large number of these sequences may have obscured the identification of unique methylated CpG islands. The methylation of high copy number sequences is not surprising, as it is consistent with the hypothesis that CpG methylation arose as a host defense mechanism (Bestor and Tycko 1996). This is particularly true of the SVA element, which is a high copy number retroposon.

However, the presence of normally methylated unique CpG islands and GC rich regions has not been observed systematically. An intriguing exception is the MAGE melanoma gene (Serrano et al. 1996), and it is thought that hypomethylation of this gene leads to its activation in cancer (De Smet et al. 1996). Our results suggest that normally methylated single-copy CpG islands and GC rich regions may be more abundant than previously believed. Indeed, the loss of methylation of such sequences may be related to gene activation in cancer, just as the gain of methylation of CpG islands and GC rich regions may lead to their silencing. Previous screens for altered CpG rich region methylation have not been designed to identify normally methylated CpG islands and GC rich regions, but it should be noted that the original observation of altered methylation in cancer was widespread loss of methylation (Feinberg and Vogelstein 1983). Furthermore, even in tumors that show increased CpG rich region methylation, the total methylation content is reduced (Feinberg et al. 1988). DNA methylation serves as an additional layer of genetic information in the genome, which has been termed the methylome (Feinberg 2001), and both increases and decreases may be important in cancer. Our strategy for cloning these sequences can be generalized to secondary libraries in addition to the Eag library, and the identification of additional such sequences thus should enhance our understanding of the methylome.

Another major result of the above Examples is the identification of novel CpG islands and GC rich regions that are methylated differentially in OT and CHM. The second (Eag) library would not identify known imprinted genes lacking Eag I sites, but it did contain the DMR of IGF2R (Wutz and Barlow, Mol. Cell Endocrinol. May 25, 1988; 140(1-2):9-14), as well as the DMR of the imprinted HYMA1 gene, suggesting that this strategy also can identify novel imprinted gene domains. One such gene was identified to date, a novel homolog of the Elongin A and Elongin A2 genes, which we term Elongin A3. Both Elongin A and Elongin A2 are known to be the active components of the transcription factor B (SIII) complex (Aso et al. 2000), that may compete for other components (Elongin B and C) with the VHL tumor suppressor gene (Kibel et al. 1995). We did not check directly for elongation activity of Elongin A3, but it contains the TFS2N motif as well as a nuclear localization signal, and the predicted protein sequence is 79% identical to that of Elongin A2, so it likely does have such a function.

It should be noted that gDMRs, even the gDMR within this novel imprinted gene, showed variable to complete methylation in somatic tissues. Such a pattern of methylation also is similar to that seen for the promoter of the imprinted gene ZNF127 (Strom et al. 1998), and for at least one methylated CpG rich region within the 11p15 imprinted gene domain. Thus, imprinted gene domains may harbor some methylated CpG islands and GC rich regions that show persistent differential methylation in somatic tissues, but also may contain other CpG islands and GC rich regions that do not show these differences in somatic tissues. Thus, it is important to compare methylation in sperm or CHM as a representation of the male germline, and OT (as eggs cannot be harvested from humans for this purpose), in the search for imprinted gene domains. The mouse is a useful adjunct and provides access to a greater variety of tissues at varying developmental stages, but there are substantial differences between human and mouse imprinting, both in the identity of the genes themselves, and in their developmental pattern of imprinting.

Several of these domains harbor multiple genes that have been implicated in cancer, and that show frequent loss of heterozygosity, including 4p16, 4q35, 10q26, 18q21, and 19p13. An imprinted tumor suppressor gene in one or more of these regions might not show conventional mutations in tumors, and thus identifying imprinted genes is an important part of tumor suppressor gene identification within these regions. The same region of 18q also has shown linkage in bipolar affective disorder, with preferential transmission through the paternal allele (McMahon et al. 1997). Furthermore, these domains appear to harbor both SMRs and gDMRs, suggesting that both types of methylated CpG islands and GC rich regions may be useful for identifying imprinted gene domains.

CpG islands and GC rich regions normally must be under selective pressure for their maintenance, as methylation leads to deamination and loss of cytosine. This is especially true in the case of the SMRs we have described, as they are methylated even in sperm DNA. In the case of gDMRs, their methylation in somatic tissues and oocyte-derived cells may be critical for suppression of nearby gene expression in spermatocyte progenitor cells. This may be particularly important for genes involved in establishing epigenetic states and in epigenetic reprogramming, as the chromatin of spermatocyte differs markedly from oocytes and somatic cells.

It also is likely that normally methylated CpG islands and GC rich regions are involved directly in chromatin formation. For example, they could serve as chromatin insulators separating enhancers from promoters. If that is so, then we would expect to find their loss of methylation in specific tissues at specific developmental stages, which would be consistent with the observation that imprinted genes can show developmental (tissue- and timing-specific) imprinting (Lee et al. 1997). Support for this idea also comes from our observation that SMRs were more frequently localized near the ends of chromosomes. Given that chromosomal ends are associated with the nuclear lamina in interphase (Cockell and Gasser 1999), the relative proximity of SMRs to the ends of chromosomes might permit their association with the nuclear lamina and chromatin proteins found within it.

Normally methylated CpG islands and GC rich regions also might promote chromatin formation. In an intriguing review, Pardo-Manuel de Villena et al. (2000) suggest that imprinting involving differences among homologous chromosomes arose under selective pressure to facilitate pairing and distinguish homologous chromosomes during meiosis. We suggest that SMRs also might enhance pairing and recombination by recruiting chromatin factors to specific locations along a given chromosome and allowing those factors to interact between homologous chromosomes. A prediction of our suggestion is that recombination frequencies in meiosis or even mitosis might be enhanced near normally methylated CpG islands and GC rich regions. Methylated CpG islands and GC rich regions also may play a role intrachromosomal compartmentalization. For example, the gDMRs lay within regions of comparatively lower CpG content (GC-poor isochores). Consistent with this idea, we have noted that most known imprinted genes also appear to lie within low isochore regions (PLAGL1, IGF2R, PEG1/MEST, SNRPN, PEG3, GNAS).

Finally, the identification of these methylated CpG islands and GC rich regions will facilitate comparison of their sequences to each other, as well as computational analysis of sequence motifs. For example, in preliminary experiments, several CTCF binding sites within at least 10 methylated CpG islands and GC rich regions have been identified. Therefore, CTCF binding may be a common feature of these sequences.

It has recently been proposed that CpG islands and GC rich regions fall into several groups, one of which represents unique CpG and generally unmethylated islands and GC rich regions associated with the 5' region of housekeeping genes, whereas another includes high-copy nongene CpG islands and GC rich regions that are dominated by Alu I repeat elements (Ponger et al. 2001). Because Alu I repeats are generally methylated and transcriptionally silent, high-copy CpG islands and GC rich regions are predicted to be methylated. Indeed, the report of Strichman-Almashanu et al. (2002) identified one of the high-copy CpG islands and GC rich regions (SVA) to be heavily methylated. This observation is not surprising given that repeat sequences provide signatures for de novo methylation, according to the host defense model (Bestor and Tycko 1996).

Strichman-Almashanu et al. (2002) also report the existence of a new class of unique CpG islands and GC rich regions that are methylated on both alleles in all tissues examined. Interestingly, these CpG islands and GC rich regions (SMRs) mapped to isochores with high GC content (>0.5), whereas the differentially methylated islands and GC rich regions (gDMRs) were concentrated in isochores with low GC content (<0.5). The class of unmethylated or differentially methylated CpG islands and GC rich regions could stand out in a CpG-less environment and provide landmarks for various recognition events, such as the initiation of chromatin condensation by TP2 during spermiogenesis (Kundu and Rao 1996). The complexity of CpG rich region compartmentalization of the mammalian genome was further emphasized by the observation that the methylated high-copy CpG islands and GC rich regions frequently localize close to telomeric ends (Strichman-Almanshanu et al. 2002), as do densely methylated nonrich region CpG stretches (Brock et al. 1999), indicating some methylation-dependent role in chromosomal integrity. This deduction is supported by the observation that DNA methyltransferase, Dnmt1, is essential for genomic stability in mouse embryonic stem cells (Chen et al. 1998).

TABLE 3

Chromosomal Location of SMRs and gDMRs

| Clone ID | Methylation pattern | Chromosomal location | Accession no. |
| --- | --- | --- | --- |
| 3-10 | SMR | 1q44 TEL | 14042537a |
| | | | 14423768 |
| | | | hCG1644736 |
| | | | hCG1724357 |
| 3-20 | SMR | 2q36 SUBTEL | 5174481a |
| | | | hCG1651464 |
| | | | hCG1656118 |
| | | | hCG1651461 |
| | | | hCG1651466 |
| 1-19 | SMR | 4p16 TEL | 3777583a |
| 1-41 | SMR | 4q35 TEL | hCG1788598a |
| | | | hCG1793025a |
| | | | hCG1787540 |
| 4-8 | SMR | 4q35 TEL | hCG1788598a |
| 3-4 | gDMR | 6q24 SUBTEL | hCG1660630a |

TABLE 3-continued

Chromosomal Location of SMRs and gDMRs

| Clone ID | Methylation pattern | Chromosomal location | Accession no. |
|---|---|---|---|
| 4-7 | SMR | 7p22 TEL | 6806913a |
| | | | hCG1747708 |
| | | | hCG1790856 |
| | | | hCG1747710 |
| 1-30 | SMR | 7q11.1 | hCG1779529a |
| | | | hCG1779527 |
| | | | hCG1789113 |
| | | | 13642872 |
| | | | 6572672 |
| 1-22 | SMR | 7q36 TEL | 11386149a |
| | | | hCG1799787 |
| 3-2 | SMR | 8p23 TEL | hCG1659058a |
| 2-5 | gDMR | 8q21.2 | 17451956 |
| | | | hCG1757665 |
| 2-48 | gDMR | 9p13 | hCG1659616 |
| 1-20 | gDMR | 10q26 TEL | 13325182a |
| | | | hCG1799063 |
| 3-12 | SMR | 10q26 TEL | 3122245a |
| | | | hCG1654478 |
| 3-30 | gDMR | 11q25 TEL | 17456499a |
| | | | hCG37607 |
| | | | hCG1745526 |
| 1-5 | SMR | 13q34 TEL | hCG20146a |
| 1-21 | gDMR | 14q32 TEL | 8393715a |
| | | | hCG21408 |
| 2-42 | gDMR | 16p13.1 | hCG15669a |
| 3-110 | SMR | 17q25 TEL | 8400736a |
| | | | 10435982 |
| 2-1 | SMR | 17q25 TEL | 1655842a |
| | | | 14149793 |
| 1-12 | SMR | 17q25 TEL | hCG1806389 |
| | | | hCG1796817 |
| 2-78 | gDMR | 18q21 | 13645769a |
| 3-8 | gDMR | 18q21 | 13645769a |
| 2-3 | SMR | 18q23 TEL | 6912444 |
| | | | 1914872 |
| | | | 5326898 |
| 1-13 | gDMR | 18q23 TEL | hCG1651089a |
| | | | 6688241 |
| | | | hCG20372 |
| | | | 1651088 |
| 1-6 | gDMR | 19p13.1 | 14249150a |
| 4-3 | SMR | 19p13.3 TEL | 9665054a |
| | | | hCG23965 |
| | | | 4506715 |
| | | | hCG1794585 |
| | | | 10732648 |
| 1-2 | SMR | 19q13.4 TEL | 12053197 |
| | | | 4505329 |
| | | | 5901994 |
| | | | 5689511 |
| | | | 7657128 |
| | | | 7657054 |
| | | | 7657130 |
| 2-4 | gDMR | 20q12 | 17484155a |
| | | | hCG1800975 |
| | | | hCG1653833 |
| | | | 13378306 |
| | | | 110743 |
| | | | 7799072 |

REFERENCES

Altschul, S. F., Gish, W., Miller, W., Myers, E. W., and Lipman, D. J. 1990. Basic local alignment search tool. J. Mol. Biol. 215: 403-410.

Antequera, F. and Bird, A. P. 1993. Number of CpG rich regions and genes in human and mouse. Proc. Natl. Acad. Sci. 90: 11995-11999.

Arima, T., Drewell, R. A., Arney, K. L., Inoue, J., Makita, Y., Hata, A., Oshimura, W., Wake, N., and Surani, M. A. 2001. A conserved imprinting control region at the HYMAI/ZAC domain is implicated in transient neonatal diabetes mellitus. Hum. Mol. Genet. 10:1475-1483.

Arima, T., Drewell, R. A., Oshimura, M., Wake, N., and Surani, M. A. 2000. A novel imprinted gene, HYMAI, is located within an imprinted domain on human chromosome 6 containing ZAC. Genomics 67: 248-255.

Aso, T., Yamazaki, K., Amimoto, K., Kuroiwa, A., Higashi, H., Matsuda, Y., kitajuma, S., and Hatakeyama, M. 2000. Identification and characterization of Elongin A2, a new member of the Elongin family of transcription elongation factors, specifically expressed in the testis. J. Biol. Chem. 275: 6546-6552.

Barlow, D. P. 1995. Gametic imprinting in mammals. Science 270: 1610-1613.

Bernardi, G. 1995. The human genome: Organization and evolutionary history. Ann. Rev. Genet. 29: 445-476.

Bestor, T. H. and Tycko, B. 1996. Creation of genomic methylation patterns. Nat. Genet. 12: 363-367.

Bird, A. P. 1986. CpG-rich rich regions and the function of DNA methylation. Nature 321: 209-213.

Bird, A. P., Taggart, M., Frommer, M., Miller, O. J., and Macleod, D. 1985. A fraction of the mouse genome that is derived from rich regions of nonmethylated, CpG-rich DNA. Cell 40: 91-99.

Brock, G. J., Charlton, J., and Bird, A. P. 1999. Densely methylated sequences that are preferentially localized at telomere-proximal regions of human chromosomes. Gene 240: 269-277.

Brock, G. J. R. and Bird, A. P. 1997. Mosaic methylation of the repeat unit of the human ribosomal RNA genes. Hum. Mol. Genet. 6: 451-456.

Choi, Y.-C., Gu, W., Hecht, N. B., Feinberg, A. P., and Chae, C.-B. 1996. Molecular cloning of mouse somatic and testis-specific H2B histone genes containing a methylated CpG rich region. DNA Cell Biol. 15: 495-504.

Cockell, M. and Gasser, S. M. 1999. Nuclear compartments and gene regulation. Curr. Opin. Genet. Dev. 9: 199-205.

Cross, S. H. and Bird, A. P. 1995. CpG rich regions and genes. Curr. Opin. Genet. Dev. 5: 309-314.

De Smet, C., De Backer, O., Faraoni, I., Lurquin, C., Brasseur, F., and Boon, T. 1996. The activation of human gene MAGE-1 in tumor cells is correlated with genome-wide demethylation. Proc. Natl. Acad. Sci. 93: 7149-7153.

Dyson, N. J. 1991. Essential molecular biology: A practical approach (ed. T. A. Brown), Vol. 2, pp. 111-156. IRL Press, Oxford.

Feinberg, A. P. 2001. Cancer epigenetics takes center stage. Proc. Natl. Acad. Sci. 98: 392-394.

Feinberg, A. P. 2001. Methylation meets genomics. Nat. Genet. 27: 9-10.

Feinberg, A. P. and Vogelstein, B. 1983. Hypomethylation distinguishes genes of some human cancers from their normal counterparts. Nature 301: 89-92.

Feinberg, A. P., Gehrke, C. W., Kuo, K. C., and Ehrlich, M. 1988. Reduced genomic 5-methylcytosine content in human colonic neoplasia. Cancer Res. 48: 1159-1161.

Ferguson-Smith, A. C., Sasaki, H., Cattanach, B. M., and Surani, M. A. 1993. Parental-origin-specific epigenetic modification of the mouse H19 gene. Nature 362: 751-755.

Gardiner-Garden, M. and Frommer, M. 1987. CpG rich regions in vertebrate genomes. J. Mol. Biol. 196: 261-282.

Hayashizaki, Y., Shibata, H., Hirotsune, S., Sugino, H., Okazaki, Y., Sasaki, N., Hirose, K., Imoto, H., Okuizumi, H., Muramatsu, M. 1994. Identification of an imprinted U2af binding protein related sequence on mouse chromosome 11 using the RLGS method. Nat. Genet. 6: 33-40.

Herman, J. G., Latif, F., Weng, Y., Lerman, M. I., Zbar, B., Liu, S., Samid, D., Duan, D. R., Gnarra, G. R., Linehan, W. M. 1994. Silencing of the VHL tumor-suppressor gene by DNA methylation in renal carcinoma. Proc. Natl. Acad. Sci. 91: 9700-9704.

Huang, T. H., Perry, M. R., and Laux, D. E. 1999. Methylation profiling of CpG rich regions in human breast cancer cells. Hum. Mol. Genet. 8: 459-470.

Kawajiri, K., Watanabe, J., Gotoh, O., Tagashira, Y., Sogawa, K., and Fujii-Kuriyama, Y. 1986. Structure and drug inducibility of the human cytochrome P-450c gene. Eur. J. Biochem. 159: 219-225.

Kibel, A., Iliopoulos, O., DeCaprio, J. A., and Kaelin, W. G., Jr. 1995. Binding of the von Hippel-Lindau tumor suppressor protein to Elongin B and C. Science 269: 1444-1446.

Kim, J., Lu, X., and Stubbs, L. 1999. Zim1, a maternally expressed mouse Kruppel-type zinc-finger gene located in proximal chromosome 7. Hum. Mol. Genet. 8: 847-854.

Kohlhase, J., Hausmann, S., Stojmenovic, G., Dixkens, C., Bink, K., Schulz-Schaeffer, W., Altmann, M., and Engel, W. 1999. SALL3, a new member of the human spalt-like gene family, maps to 18q23. Genomics 62: 216-222.

Larsen, F., Gundersen, G., Lopez, R., and Prydz, H. 1992. CpG rich regions as gene markers in the human genome. Genomics 13: 1095-1107.

Lee, M. P., Hu, R.-J., Johnson, L. A., and Feinberg, A. P. 1997. Human KVLQT1 gene shows tissue-specific imprinting and encompasses Beckwith-Wiedemann syndrome chromosomal rearrangements. Nat. Genet. 15: 181-185.

McMahon, F. J., Hopkins, P. J., Xu, J., McInnis, M. G., Shaw, S., Cardon, L., Simpson, S. G., MacKinnon, D. F., Stine, O. C., Sherrington, R. 1997. Linkage of bipolar affective disorder to chromosome 18 markers in a new pedigree series. Am. J. Hum. Genet. 61: 1397-1404.

Merlo, A., Herman, J. G., Mao, L., Lee, D., Gabrielson, E., Burger, P. C., Baylin, S. B., and Sidransky, D. 1995. 5' CpG rich region methylation is associated with transcriptional silencing of the tumour suppressor p16/CDKN2/MTS1 in human cancers. Nat. Med. 1: 686-692.

Ohlsson, R., Renkawitz, R., and Lobanenkov, V. 2001. CTCF is a uniquely versatile transcription regulator linked to epigenetics and disease. Trends Genet. 17: 520-527.

Pardo-Manuel de Villena, F., de la Casa-Esperon, E., and Sapienza, C. 2000. Natural selection and the function of genome imprinting: Beyond the silenced minority. Trends Genet. 16: 573-579.

Plass, C., Shibata, H., Kalcheva, I., Mullins, L., Kotelevtseva, N., Mullins, J., Kato, R., Sasaki, H., Hirotsune, S., Okazaki, Y. 1996. Identification of Grf1 on mouse chromosome 9 as an imprinted gene by RLGS-M. Nat. Genet. 14: 106-109.

Razin, A. and Cedar, H. 1994. DNA methylation and genomic imprinting. Cell 77: 473-476.

Serrano, A., Garcia, A., Abril, E., Garrido, F., and Ruiz-Cabello, F. 1996. Methylated CpG points identified within MAGE-1 promoter are involved in gene repression. Int. J. Cancer 68: 464-470.

Shen, L., Wu, L. C., Sanlioglu, S., Chen, R., Mendoza, A. R., Dangel, A. W., Carroll, M. C., Zipf, W. B., and Yu, C. Y. 1994. Structure and genetics of the partially duplicated gene RP located immediately upstream of the complement C4A and the C4B genes in the HLA class III region. Molecular cloning, exon-intron structure, composite retroposon, and breakpoint of gene duplication. J. Biol. Chem. 269: 8466-8476.

Shiraishi, M., Chuu, Y. H., and Sekiya, T. 1999. Isolation of DNA fragments associated with methylated CpG rich regions in human adenocarcinomas of the lung using a methylated DNA binding column and denaturing gradient gel electrophoresis. Proc. Natl. Acad. Sci. 96: 2913-2918.

Stine, O. C., Xu, J., Koskela, R., McMahon, F. J., Gschwend, M., Friddle, C., Clark, C. D., McInnis, M. G., Simpson, S. G., and Breschel, T. S. 1995. Evidence for linkage of bipolar disorder to chromosome 18 with a parent-of-origin effect. Am. J. Hum. Genet. 57: 1384-1394.

Strom, T. M., Hortnagel, K., Hofmann, S., Gekeler, F., Scharfe, C., Rabl, W., Gerbitz, K. D., and Meitinger, T. 1998. Diabetes insipidus, diabetes mellitus, optic atrophy and deafness (DIDMOAD) caused by mutations in a novel gene (wolframin) coding for a predicted transmembrane protein. Hum. Mol. Genet. 7: 2021-2028.

Toyota, M., Ho, C., Ahuja, N., Jair, K.-W., Li, Q., Ohe-Toyota, M., Baylin, S. B., and Issa, J.-P. J. 1999. Identification of differentially methylated sequences in colorectal cancer by methylated CpG rich region amplification. Cancer Res. 59: 2307-2312.

Wang, A. H., Kruhlak, M. J., Wu, J., Bertos, N. R., Vezmar, M., Posner, B. I., Bazett-Jones, D. P., and Yang, X. J. 2000. Regulation of histone deacetylase 4 by binding of 14-3-3 proteins. Mol. Cell. Biol. 20: 6904-6912.

Yen, P. H., Patel, P., Chinault, A. C., Mohandas, T., and Shapiro, L. 1984. Differential methylation of hypoxanthine phosphoribosyltransferase genes on active and inactive human X chromosomes. Proc. Natl. Acad. Sci. 81: 1759-1763.

Zhu, Z. B., Hsieh, S., Bently, D. R., Campbell, D. R., and Volanakis, J. E. 1992. A variable number of tandem repeats locus within the human complement C2 gene is associated with a retroposon derived from a human endogenous retrovirus. J. Exp. Med. 175: 1783-1787.

Bestor, T. and Tycko, B. 1996. Nat. Genet. 12: 363-367.

Brandeis, M., Frank, D., Keshet, I., Siegfried, Z., Mendelsohn, M., Nemes, A., Temper, V., Razin, A., and Cedar, H. 1994. Nature 371: 435-438.

Brock, G., Charlton, J., and Bird, A. 1999. Gene 240: 269-277.

Chen, R., Pettersson, U., Beard, C., Jackson-Grusby, L., and Jaenisch, R. 1998. Nature 395: 89-93.

Cross, S, and Bird, A. 1995. Curr. Opin. Genet. Dev. 5: 309-314.

De Smet, C., De Backer, O., Faraoni, I., Lurquin, C., Brasseur, F., and Boon, T. 1996. Proc. Natl. Acad. Sci. 93: 7149-7153.

Feinberg, A. and Vogelstein, B. 1983. Nature 301: 89-94.

Hejnar, J., Hajkova, P., Plachy, J., Elleder, D., Stepanets, V., and Svoboda, J. 2001. Proc. Natl. Acad. Sci. USA 98: 565-569.

Issa, J.-P. J. and Baylin, S. B. 1996. Nat. Med. 2: 281-282.

Kundu, T. and Rao, M. 1996. Biochemistry 35: 15626-15632.

Macleod, D., Charlton, J., Mullins, J., and Bird, A. P. 1994. Genes Dev. 8: 2282-2292.

Ohlsson, R., Cui, H., He, L., Pfeifer, S., Jiang, S., Feinberg, A. P., and Hedborg, F. 1999. Cancer Res. 59: 3889-3892.

Ohlsson, R., Renkawitz, R., and Lobanenkov, V. 2001. Trends Genet. 17: 520-527.

Ponger, L., Duret, L., and Mouchiroud, D. 2001. Genome Res. 11: 1854-1860.

Razin, A. and Cedar, H. 1994. Cell 77: 473-476.

Strichman-Almanshanu, L., Lee, R., Onyango, P., Perlman, E., Flam, F., Frieman, M., and Feinberg, A. 2002. Genome Res. X, Y. (incorporated herein by reference in its entirety).

Voo, K. S, Carlone, D. L., Jacobsen, B. M., Flodin, A., and Skalnik, D. G. 2000. Mol. Cell. Biol. 20: 2108-2121.

Yan, P., Chen, C., Shi, H., Rahmatpanah, F., Wei, S., Caldwell, C., and Huang, T. 2001. Cancer Res. 61: 8375-8380.

Although the invention has been described with reference to the above examples, it will be understood that modifications and variations are encompassed within the spirit and scope of the invention. Accordingly, the invention is limited only by the following claims.

What is claimed is:

1. A method for determining the DNA methylation status of a combination of DNA sequences from a genomic DNA sample comprising determining the methylation status of a combination of DNA sequences, wherein the sequences consist of SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:16, SEQ ID NO:21, SEQ ID NO:22, SEQ ID NO:23, SEQ ID NO:26, SEQ ID NO:29, and SEQ ID NO:30.

2. The method of claim 1, wherein determining the methylation status comprises use of a methylation-sensitive restriction enzyme.

3. The method of claim 2, wherein the methylation-sensitive restriction enzyme is one or more of SmaI, SacII, EagI, MspI, HpaII, BstUI and BssHII.

4. The method of claim 1, wherein determining the methylation status comprises a methylation-specific polymerase chain reaction (MSP).

5. The method of claim 1, wherein determining the methylation status comprises use of bisulfite.

6. The method of claim 1, wherein the sample is from a subject known to have cancer.

7. The method of claim 1, wherein the methylation status is hypomethylation.

8. The method of claim 1, further comprising cleaving the genomic DNA with both a restriction endonuclease that cleaves at a recognition site comprising adenosine and thymidine residues and a restriction endonuclease that cleaves at an unmethylated restriction site comprising cytidine and guanosine residues.

9. The method of claim 1, wherein determining the methylation status comprises detecting hybridization of one or more oligonucleotide probes.

10. The method of claim 9, wherein the oligonucleotide probe is detectably labeled.

11. The method of claim 1, wherein the genomic DNA sample is human.

* * * * *

SEQUENCE LISTING

<160> NUMBER OF SEQ ID NOS: 33

<210> SEQ ID NO 1
<211> LENGTH: 1641
<212> TYPE: DNA
<213> ORGANISM: Homo sapiens

<400> SEQUENCE: 1

```
atggcggcag ggtccactac gctgcgcgca gtggggaagc tgcaggtgcg tctggccact      60
aagacggagc cgaaaaagct agagaaatat ttgcagaaac tctccgcctt gcccatgacc     120
gcagacatcc tggcggagac tggaatcaga aagacggtga agcgcctgcg gaagcaccag     180
cacgtgggcg acttttgccag agacttagcg gcccggtgga agaagctggt gctcgtggac    240
cgaaacaccg ggcctgaccc gcaggaccct gaggagagcg cttcccgaca gcgcttcggg     300
gaggctcttc aggagcggga aaaggcctgg ggcttcccag aaaacgcgac ggcccccagg     360
agcccatctc acagccctga gcacagacgg acagcacgca gaacacctcc ggggcaacag     420
agacctcacc cgaggtctcc cagtcgcgag cccagagcca agagaaagcg ccccagaatg     480
gccccagctg attccggccc ccatcgggac cctcaacgc gcaccgctcc cctcccgatg      540
cccgagggcc ctgagcccgc tgtgcccggg gagcaacccg gaagaggcca cgctcacgcc     600
gctcagggcg ggcctctgct gggtcaaggc tgccagggcc aaccccaggg ggaagcggtg     660
gggagccaca gcaaggggca caaatcgtcc cgcggggctt cggctcagaa atcgcctcct    720
gtccaggaaa gccagtcaga gaggctgcag gcggccggcg ctgattccgc cgggccgaaa    780
acggtgccca gccatgtctt ctcggagctc tgggacccct cagaggcctg gatgcaggcc    840
aactacgatc tgctgtccgc ttttgaggcc atgacctccc aggcaaaccc agaagcactc    900
tgcgcgccag cgctccagga ggaagctgct ttccctggac gcagagtgaa cgctaagatg     960
ccggtgtact cgggctccag gcctgcctgc cagctccagg tgccgacgct gcgccagcag    1020
tgcctccggg tgcctaggaa caatccggac gccctcggcg acgtggaagg ggtcccctac    1080
tcggttcttg aaccgttcct ggaagggtgg acgcccgatc agctgtaccg cacagagaaa    1140
gacaatgccg cactcgctcg agagacagat gaattatgga ggattcattg cctccaggac    1200
ttcaaggaag aaaagccaca ggagcacgag tcttggcggg agctgtacct gcggcttcgg    1260
gacgcccgag agcagcggct gcgagtagtg accacgaaaa tccgatccgc acgtgaaaac    1320
aaacccagcg gccgacagac aaagatgatc tgtttcaact ctgtggccaa gacgccttat   1380
gatgcttcca ggaggcaaga gaagtctgca ggagccgctg accccggaaa tggagagatg    1440
gagccagccc ccaagcccgc aggaagcagc caggctccct ccggcctcgg ggacggcgac    1500
ggcggcagcg tgacgcgcgg cggcagcagc aaccggcacg cggcgcccgc ggacaaaacc    1560
cgaaaacagg ctgccaagaa agtggccccg ctgatggcca aggcaattcg agactacaag    1620
```
ggaagattct cccgacgata a        1641

<210> SEQ ID NO 2
<211> LENGTH: 546
<212> TYPE: PRT
<213> ORGANISM: Homo sapiens

<400> SEQUENCE: 2

Met Ala Gly Ser Thr Thr Leu Arg Ala Val Gly Lys Leu Gln Val
1               5                   10                  15

Arg Leu Ala Thr Lys Thr Glu Pro Lys Lys Leu Glu Lys Tyr Leu Gln
            20                  25                  30

Lys Leu Ser Ala Leu Pro Met Thr Ala Asp Ile Leu Ala Glu Thr Gly
        35                  40                  45

Ile Arg Lys Thr Val Lys Arg Leu Arg Lys His Gln His Val Gly Asp
    50                  55                  60

Phe Ala Arg Asp Leu Ala Ala Arg Trp Lys Lys Leu Val Leu Val Asp
65                  70                  75                  80

Arg Asn Thr Gly Pro Asp Pro Gln Asp Pro Glu Glu Ser Ala Ser Arg
                85                  90                  95

Gln Arg Phe Gly Glu Ala Leu Gln Glu Arg Glu Lys Ala Trp Gly Phe
            100                 105                 110

Pro Glu Asn Ala Thr Ala Pro Arg Ser Pro Ser His Ser Pro Glu His
        115                 120                 125

Arg Arg Thr Ala Arg Arg Thr Pro Pro Gly Gln Gln Arg Pro His Pro
    130                 135                 140

Arg Ser Pro Ser Arg Glu Pro Arg Ala Glu Lys Arg Pro Arg Met
145                 150                 155                 160

Ala Pro Ala Asp Ser Gly Pro His Arg Asp Pro Pro Thr Arg Thr Ala
                165                 170                 175

Pro Leu Pro Met Pro Glu Gly Pro Glu Pro Ala Val Pro Gly Glu Gln
            180                 185                 190

Pro Gly Arg Gly His Ala His Ala Ala Gln Gly Gly Pro Leu Leu Gly
        195                 200                 205

Gln Gly Cys Gln Gly Gln Pro Gln Gly Glu Ala Val Gly Ser His Ser
    210                 215                 220

Lys Gly His Lys Ser Ser Arg Gly Ala Ser Ala Gln Lys Ser Pro Pro
225                 230                 235                 240

Val Gln Glu Ser Gln Ser Glu Arg Leu Gln Ala Gly Ala Asp Ser
                245                 250                 255

Ala Gly Pro Lys Thr Val Pro Ser His Val Phe Ser Glu Leu Trp Asp
            260                 265                 270

Pro Ser Glu Ala Trp Met Gln Ala Asn Tyr Asp Leu Leu Ser Ala Phe
        275                 280                 285

Glu Ala Met Thr Ser Gln Ala Asn Pro Glu Ala Leu Cys Ala Pro Ala
    290                 295                 300

Leu Gln Glu Glu Ala Ala Phe Pro Gly Arg Arg Val Asn Ala Lys Met
305                 310                 315                 320

Pro Val Tyr Ser Gly Ser Arg Pro Ala Cys Gln Leu Gln Val Pro Thr
                325                 330                 335

Leu Arg Gln Gln Cys Leu Arg Val Pro Arg Asn Asn Pro Asp Ala Leu
            340                 345                 350

Gly Asp Val Glu Gly Val Pro Tyr Ser Val Leu Glu Pro Val Leu Glu
        355                 360                 365

| | | | | | | | | | | | |
|---|---|---|---|---|---|---|---|---|---|---|---|
| Gly | Trp | Thr | Pro | Asp | Gln | Leu | Tyr | Arg | Thr | Glu | Lys | Asp | Asn | Ala | Ala |
| | | 370 | | | | 375 | | | | 380 | |

Gly Trp Thr Pro Asp Gln Leu Tyr Arg Thr Glu Lys Asp Asn Ala Ala
            370                 375                 380

Leu Ala Arg Glu Thr Asp Glu Leu Trp Arg Ile His Cys Leu Gln Asp
385                 390                 395                 400

Phe Lys Glu Glu Lys Pro Gln Glu His Glu Ser Trp Arg Glu Leu Tyr
                405                 410                 415

Leu Arg Leu Arg Asp Ala Arg Glu Gln Arg Leu Arg Val Val Thr Thr
                420                 425                 430

Lys Ile Arg Ser Ala Arg Glu Asn Lys Pro Ser Gly Arg Gln Thr Lys
                435                 440                 445

Met Ile Cys Phe Asn Ser Val Ala Lys Thr Pro Tyr Asp Ala Ser Arg
            450                 455                 460

Arg Gln Glu Lys Ser Ala Gly Ala Ala Asp Pro Gly Asn Gly Glu Met
465                 470                 475                 480

Glu Pro Ala Pro Lys Pro Ala Gly Ser Ser Gln Ala Pro Ser Gly Leu
                485                 490                 495

Gly Asp Gly Asp Gly Gly Ser Val Ser Gly Gly Ser Ser Asn Arg
            500                 505                 510

His Ala Ala Pro Ala Asp Lys Thr Arg Lys Gln Ala Ala Lys Lys Val
            515                 520                 525

Ala Pro Leu Met Ala Lys Ala Ile Arg Asp Tyr Lys Gly Arg Phe Ser
530                 535                 540

Arg Arg
545

<210> SEQ ID NO 3
<211> LENGTH: 641
<212> TYPE: DNA
<213> ORGANISM: Homo sapiens
<220> FEATURE:
<221> NAME/KEY: misc_feature
<222> LOCATION: (360)..(629)
<223> OTHER INFORMATION: n is any nucleotide

<400> SEQUENCE: 3

```
cggccggcgc ttcccgcacc tcccggcgct gctgctacac cggcgccgcc agcatctgcc      60
agagcggccc cgccgctgcc cgctgtgcgc ccgcaccttc cggcagagcg cgctgctctt     120
ccaccaggcg cgggcgcacc ccttggggac aactctgac  cctgctgccc caccccaccg     180
ctgcgcgcag tgcccgcgag ccttccgaag cggcgccggg ctgcggagtc acgcgcgcat     240
ccacgtgtcc cggagcccca cgcgaccccg tgtctcagac gcccaccagt gtggcgtgtg     300
cggcaagtgc tttggcaaga gctctacgct gacgcgacac ctgcaacgca ctcgggggan     360
aaaccctnna gnngcccgan tgnggnaagg gcttctggag agcccacgct ggtgcgccac     420
cagcgcacac acacnggcga aaagccgtac gcatgtggcg actgtggacg ctgttnagcg     480
agagttccac gcttnttgcg ccatcggcgc anccataag  ggcgagcggn cacatgcgtg     540
cgccacttgc ggnaagggtt tcgggcagcg ctccacctgg tggtgcacca gcgcattcac     600
acnggcgaag aagcctttgc gtgccccgna gtggcgggcg g                        641
```

<210> SEQ ID NO 4
<211> LENGTH: 113
<212> TYPE: DNA
<213> ORGANISM: Homo sapiens

<400> SEQUENCE: 4

```
cggcccgcgt tatatgacat tccacgttat gtgacattcc ggtgtgccgg cgtgtggccg      60
```

```
cgttatatga cattccacgt tatgtgacat tccggtgtgc tggcgtgcgg ccg        113
```

<210> SEQ ID NO 5
<211> LENGTH: 149
<212> TYPE: DNA
<213> ORGANISM: Homo sapiens

<400> SEQUENCE: 5

```
cggccgcttc aagtacgtcc gcgtgactga catcgacaac agcgccgagt ctgccatcaa   60
catgctcccg ttcttcatcg gcgactggat gcgctgcctc tacggcgagg cctaccctgc  120
ctgcagccct ggcaacacct ccacggccg                                    149
```

<210> SEQ ID NO 6
<211> LENGTH: 399
<212> TYPE: DNA
<213> ORGANISM: Homo sapiens

<400> SEQUENCE: 6

```
cggccgcctc tgacgcgccc cctcttttgt ttcgcccgca gcccatcttc ggagtccagc   60
agcaagtggc gcggcaggcc aaggccttcc tgtcgctggg aaagatggcc gaggtgcagg  120
tgagccggcg ccgggccggc ggcgcgcagt cctggctgtg ttcgccacgg tcaagtcgct  180
gatcggcaag ggcgtcatgc tggccgtcag ccagggccgc gtgcagacca acgtgctcaa  240
catcgccaac gaggactgca tcaaggtggc ggccgtgctc aacaacgcct ctacctgga   300
gaacctgcac ttcaccatcg agggcaagga cacgcactac ttcatcaaga ccaccacgcc  360
cgagagcgac ctgggcacgc tgcggttgac cagcggccg                         399
```

<210> SEQ ID NO 7
<211> LENGTH: 130
<212> TYPE: DNA
<213> ORGANISM: Homo sapiens

<400> SEQUENCE: 7

```
cggccgtgct caacaacgcc ttctacctgg agaacctgca cttcaccatc gagggcaagg   60
acacgcacta cttcatcaag accaccacgc ccgagagcga cctgggcacg ctgcggttga  120
ccagcggccg                                                         130
```

<210> SEQ ID NO 8
<211> LENGTH: 428
<212> TYPE: DNA
<213> ORGANISM: Homo sapiens
<220> FEATURE:
<221> NAME/KEY: misc_feature
<222> LOCATION: (228)..(412)
<223> OTHER INFORMATION: n is any nucleotide

<400> SEQUENCE: 8

```
cggccgcgcc gttccggctc ccgagccccg cctgcgcgcg gcctcctcgg cgcagccatc   60
ctcttggctg ccgcgggcgg caaagcccac ggcatctgcc atttgtcatt cagcccgtcg  120
gtaccgcccc gagccttgat ttagacacgg ctggggcgtg ctctggcctc actctccggg  180
cgggtgctgg acggacggac ggacggggca gccgtgctca cagctcanca gcgcggggcc  240
ttggcgcgcg gggcgctttc ccgggtcgcc gtcatggccg cggaggtgga cgcccgagcg  300
gnctcgcctg agctccgggg gtcgtcgccc cgcaaggtag nttttgggtg ctcccgcttc  360
ggcgggccgg cttgggggca acggtggccn ggcattgccc gctgcgaaga cngccttggt  420
tccggccg                                                           428
```

<210> SEQ ID NO 9
<211> LENGTH: 204
<212> TYPE: DNA
<213> ORGANISM: Homo sapiens

<400> SEQUENCE: 9
cggccgtcag ccatcgtaat gacatgtctg tgggttgccc tgtgccgcca ggctgggctg    60
tcggaagcac ccagcgacgt gtctgtgggt ccgccccgtg ccgccaggcc gggccatcgg   120
aaacacctgc agtaaccgga gtgccctcgc tgatagccct tgttccgggg cctcgtcctg   180
ggctgtgcag agctccagcc ctag                                          204

<210> SEQ ID NO 10
<211> LENGTH: 126
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is any nucleotide

<400> SEQUENCE: 10
cggccgccac agccgccgcc atcttcttcc tgcccttgcc ttggtgggtg gcggtttcct    60
gcgccgtgtc tggcttggcc agccggagca ccgcgctggg ctccatgcag ccgggctgcg   120
cggccg                                                              126

<210> SEQ ID NO 11
<211> LENGTH: 125
<212> TYPE: DNA
<213> ORGANISM: Homo sapiens

<400> SEQUENCE: 11
cggccgtggg aagtacgcga ggcaggggggg tggccgtggg agggacgcga ggcaggggggc    60 ggctgtggga gggacttgag gcagggaggt ggccctggga gggacttgag gcaggggtc   120 ggccg                                                               125

<210> SEQ ID NO 12
<211> LENGTH: 669
<212> TYPE: DNA
<213> ORGANISM: Homo sapiens
<220> FEATURE:
<221> NAME/KEY: misc_feature
<222> LOCATION: (593)..(630)
<223> OTHER INFORMATION: n is any nucleotide

<400> SEQUENCE: 12
ccccacaccc tcctcagcat ttgccgtctg tgtccacgcg actgccccac gccctcctta    60
gcatttgcca tccatgccca tgtggccgcc ccacgccctc ctcagcattt gccctctgtg   120
tccctgcggc tagccaatgc cctcctcagc atttgccctc tgtgtccacg tggccgcccc   180
acaccctcct cagcatttgc cctctgtgtc catgcagccg gccacgccc tcctcagcat   240 ttgccctctg tgtccacgca gccggccac gccctcctca gcatttgccc tctgtgtcca   300
tgcagccggc ccacgccctc ctcagcattt gccctctgtg tccacgcagc cggcccacgc   360
cctcctcagc atttgccctc tgtgtccacg cagccggccc acgccctcct cagcatttgc   420
cctctgtgtc cacatggtcg ccccacgccc tcctcagcat ttgctgtctg tgtccacgtg   480
gccgccaagc cctcctcagc atttgctgtt gtccacgcag ccggccacgc cctcctcagc   540
atttgccctc tatgtcacgt ggccgcccac gccctctcag aatttgctgc tgngacacgt   600

```
ggcaccccat gccctcttaa gatttgcatn catgcccacg tggcacccca cgcccttctt    660
aagatttgc                                                            669

<210> SEQ ID NO 13
<211> LENGTH: 383
<212> TYPE: DNA
<213> ORGANISM: Homo sapiens
<220> FEATURE:
<221> NAME/KEY: misc_feature
<222> LOCATION: (119)..(119)
<223> OTHER INFORMATION: n is any nucleotide

<400> SEQUENCE: 13
cggccgcaag gagagcctcg atggcttcgt ggagaccttc aagaaagagt tgtccagaga     60
cgcttatcca ggaatctacg ccttggactg tgagatgtgc tacaccacgc atggcctana    120
gctgacccgc gtcaccgtgg tggacgccga catgcgagtg gtgtacgaca ccttcgtcaa    180
gcccgacaac gagatcgtgg actacaacac caggttttcc ggagtcaccg aggccgacgt    240
cgccaagacg agcatcacgt tgccccaagt ccaagccatc ctgctgagct ttttcagcgc    300
ccaaaccatc ctcatcgggc acagcctgga gagcgacctg ctggccctga agctcatcca    360
cagcaccgtg gtggacacgg ccg                                            383

<210> SEQ ID NO 14
<211> LENGTH: 1123
<212> TYPE: DNA
<213> ORGANISM: Homo sapiens
<220> FEATURE:
<221> NAME/KEY: misc_feature
<222> LOCATION: (31)..(59)
<223> OTHER INFORMATION: n is any nucleotide

<400> SEQUENCE: 14
taaaccaatt tcacaggcaa gtttcccttg aaaaacaact ccttgccata atcatcacat     60
tcattgagtg accatctacc aaatgcttta ctcccatgat ttcatgtaat attgacattc    120
accctacaaa gtagatggta ttacagtgtc tgttttacaa gtgagaaatc cgaggaacag    180
gaagtcaatt tgccaagtgt tgcacagcta atcgagatt ccagagaatg tcacctcaaa    240
gcttctagtg gggctgtcat gtaggttgtg gtcgctttgg ataacaggag acgctaagga    300
aaatcagtac tggttactga ggatggaaga ggcgcarata tttccaccac ggcgacgaaa    360
accccacttt taggctggcc acacaggagc cccgaggaaa ctatgcgtcc ccttcctccc    420
cgcccccaca ctgccctggc ctggcggagc agcggccgca agtgtaactg ttgttgccca    480
gatcgaacca agcccggtcc cagtgacgag cagcggcctg cggggccaga gcgtctggga    540
gcctttcatg accccaaagc ccaggaggt ccccgcacca tcgggcccg cgccctagct    600 cggtccgccg tcgagggtgc ctgaagtccc ctgcgggcgc cggggagaaa gcccggggct    660
tagcctcctc catccccagc catctgtcac cgcctcctag gccccggctg gagccccatg    720
ggcgcctccc gcgcctacca aggagccagg gagacaagga tcccggagac ctctggggcg    780
ccctccagct gaggattccg ccgcggctcc cgcagccgct tctccccatt cggtgcagcc    840
cacctggccc agctctcggc cggtctccct cggaggtccg aaaagggaga gggcgggcca    900
gggctccccg ctggccggag ccgcagcccc tttccccctc ccccacccag ggacccttcc    960
cggaccctcc tgggcgcagc cctcacctgc tgcccgcacc gcctccgagg aaggccctcg   1020
ggctccacct ggcctcatca ccgcttccct tatccgggag gaggaggaaa ctcaaccctc   1080
taggccaggc cctgtgctca ctttagatac tttatttcgt tta                    1123
```

<210> SEQ ID NO 15
<211> LENGTH: 107
<212> TYPE: DNA
<213> ORGANISM: Homo sapiens

<400> SEQUENCE: 15
cggccgcagc cacgcgcagg gaggagcccg gggcaccata gcacagcgcc ggcctcacac    60
acaccctcga ggcccctctc gagcccccgc ggagccctcc gcggccg                 107

<210> SEQ ID NO 16
<211> LENGTH: 89
<212> TYPE: DNA
<213> ORGANISM: Homo sapiens

<400> SEQUENCE: 16
gcggccgggg acccacgcca tggtgccggg ctatgggtgt ggggtcagcc agggacccac    60
aacatcgcac tggcctgtgg ggtcggccg                                      89

<210> SEQ ID NO 17
<211> LENGTH: 914
<212> TYPE: DNA
<213> ORGANISM: Homo sapiens

<400> SEQUENCE: 17
cggccgttct ctgttacctc tctctggaga ccccggcttc tcccctgaag gcctgggagc    60
ctcacccacg gcctggcccg gagagcggtc gtgatgagga tcaaaagaag caaggctgtg   120
gctgggacag ggcactgctc ggaggcccgc cctggaggca ggcggccacc agccttctct   180
ctccttcccg cactttctcc gggccccggt cgcaggacc agcgggcagc cttggctctg    240
gggcgccctc ctttctccct gcagcccag gcggcttcc ggggctgcg cttcctcccc     300 agccaaggac agcgctcacc cgcgcccag tccccacgca ccagctgtgc agccgccgcc   360
gcctctctcg tctccgtcca gtgagttctc cgcactgcag agggcgagat cccgaaggcc   420
tggatccgcg cagaagcagg gagcaccttc catggccgcc gccatcctca gcaccgtccc   480
gcggctgccc ccatcctcag caccggaagg aaaaccaggc cgccgccatc ctcagcaccg   540
gaaggaaaac caggccgccg ccatcctcag caccggaagg aaaaccgggc cgcagcacgg   600
ccttgttggg ctccctccga gctctctgcc gccttcatga tccagccccg gtctgacccc   660
cgcctccttt ctggcctttg ttccaccccc tgtctgagcc ttccccagtc cggactcgag   720
gccgctctgt gcaatgccac ccttcgctac cccgcctggt ccagcggatc cgcccccagc   780
ctctccaggc cggcgcctcc tctaccggga ctcagctgcg cgctcctcaa cgggcctccc   840
cggcggcgtc tgcgctgctg gagtcggcgt ccggctcctc ccgagcaccg gggctcctgc   900
gggctccgcg gccg                                                      914

<210> SEQ ID NO 18
<211> LENGTH: 229
<212> TYPE: DNA
<213> ORGANISM: Homo sapiens

<400> SEQUENCE: 18
cgggctcggg gtcagggtgg gcagtggaca ctcacgcaac atggaggacc tacagccgcg    60
ggctcggggt cagggcaggc agtggacgct cacacacaga ggacctacag ccgcgggctc   120
agggtcaggg cggacagtgg atgcccacac aacacagagg acctacgcc acaggctcgg    180 ggtcagggcg ggcagtggat gcccacacaa cacggaggac ctgcggccg                229

```
<210> SEQ ID NO 19
<211> LENGTH: 141
<212> TYPE: DNA
<213> ORGANISM: Homo sapiens

<400> SEQUENCE: 19
cggccgagat tcctacgaa gaggccctga ggagggcccg gcgcggtcgc cgggagaatg      60
tggggctgta ccccgcgcct gtgcctctgc cctacgccag cccctacgcc tacgtggcta    120
gcgactccga gtactcggcc g                                              141

<210> SEQ ID NO 20
<211> LENGTH: 788
<212> TYPE: DNA
<213> ORGANISM: Homo sapiens

<400> SEQUENCE: 20
cggccggggg gcccctgggg agctaggccg ggctcgggca caggcaccgg cacgggcact     60
ggcaccggca ccggcacggg caagggcacc gacccgacgg cggtgggcgc gggccgggag    120
ccgctgccgc tctcggtcag caccgtccgc ttgagcggcc caggcgcctc gaggcgcagt    180
ggcccggcgg cgggcgggcg gtccccgggg ggcttgcgcg cgcggtgcga gggccggcgg    240
cgcagctcgg acgtgagctc gtgcttgagg aagcggaaca cctccttggc tgggccgcgg    300
cgctcgggct ccagggccag taagcgctgg aacatgcgca gcgcgggctc ggtgaagcgg    360
cgccactgcg aaggcagccc cggcaggcgg ccccgctgcc agcgcacgaa ctcctcgaag    420
aaggcgtcgg cgcccgacgc cgcctcccac ggaagttgcc ggtgagcacg cagaagatga    480
gcacgccgaa ggcccacacg tccacgcccg tgtccaccgc cagcccgtcg gcgcggcccg    540
cctggcacac ctcaggcgcc gtgtaaggga tggtgccgct cacgcgcttg acgcggcagc    600
ccacgcggcg cgtcatgccg aagtcggcca gctttacgcg gcggcactcg cggtcgaaca    660
gcagcacgtt ctcgggcttg atgtcgcggt gcaccagctg ccgcccgtgc atgaagtcca    720
gcgccaggcc cagctgctgc acacagcgct tcaccgtgtc ctcagggagc cccacctgcg    780
ggcggccg                                                             788

<210> SEQ ID NO 21
<211> LENGTH: 154
<212> TYPE: DNA
<213> ORGANISM: Homo sapiens

<400> SEQUENCE: 21
cggccgcatt ttatagtcag acacaaccac aacatggttg tgaccgggca gtcgaaccct     60
caggatcgac ccaagagaca tgaaactacc cacacaaagg ctgctatggg aacatgcacg    120
acactcctcc ttcctaatag ccaaaacacg gccg                                154

<210> SEQ ID NO 22
<211> LENGTH: 677
<212> TYPE: DNA
<213> ORGANISM: Homo sapiens
<220> FEATURE:
<221> NAME/KEY: misc_feature
<222> LOCATION: (101)..(632)
<223> OTHER INFORMATION: n is any nucleotide

<400> SEQUENCE: 22
cggccgacgg tggtgtactg agcggccagg tcggctcggg ctgccggggt gttggggacg     60
aagtaaggca cctggggcag gcggtgggga gccaggctta naacaggcac cggggagcg    120
```

```
gtgtccagcc ttctccccgg ggcctcctgc aaatgggtta gcccanaaca gcctcactcc      180
ggaccacccc gtctctctac ggttctctct gtggccccga ggttgggaac ctgaatccga      240
tttggtcaga gcctctttct tcatcatcta gggccagggc tgcaagctcg taggaggcca      300
gggtccccga cccagggctg acgggcgtcc tgaaacacgg gaggggccgt cctaccagca      360
cgtccagtgg gtcgtaggcc tgggggtcc agtctgggat acgacccatg ccgctctctt      420
cgtttgcaaa cttctcacaa aangttncct actggggctg ggantgccca cagcggtggg      480
ggtcgtggga aagccaccta aaagaaanaa aggccttcac nggaagangt tnattgncaa      540
ggctgcgggg ccacttgcca cgtggcacaa gaaanccctc nggttttgcc tcttcttttg      600
ttttggaant naacctgtga ncctaattgc tnaagtttcc cattttcctt tttcccttg      660 accaagctta acttaat                                                    677

<210> SEQ ID NO 23
<211> LENGTH: 110
<212> TYPE: DNA
<213> ORGANISM: Homo sapiens

<400> SEQUENCE: 23
cggccgtgtg ggcatccgtg tcagagtgct gtgtgccggg cgacgctcag ggcggctgtg       60
cgggcatctg tgtcagagtg ctgtgtgccg ggcgacgctc agggcggccg                  110

<210> SEQ ID NO 24
<211> LENGTH: 1578
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is any nucleotide

<400> SEQUENCE: 24
cggccgctgg gtttgttttc acgtgcggat cggattttcg tggtcactac tcgcagncgc       60
tgctctcggg cgtcccgaag ccgcaggtac agctcccgcc aagactcgtg ctcctgtggc      120
ttttcttcct tgaagtcctg gaggcaatga atcctccata attcatctgt ctctcgagcg      180
agtgcggcat tgtctttctc tgtgcggtac ggctgatcgg gcgtccaccc ttccagaacg      240
ggttcaagaa ccgagtaggg gaccccttcc acgtcgccga gggcgtccgg attgttccta      300
ggcacccgga ggcactgctg gcgcagcgtc ggcacctgga gctggcaggc aggcctggag      360
cccgagtaca ccggcatctt agcgttcact ctgcgtccag ggaaagcagc ttcctcctgg      420
agcgttggcg cggagagtgc ttctgggttt gcctgggagg tcatggcctc aaaagcggac      480
agcagatcgt agttggcctg catccaggcc tctgaggggt cccagagctc cgagaagaca      540
tggctgggca ccgttttcgg cccggcggaa tcaagcgccg ccgcctgca gcctctctga      600 ctggctttcc tggacaggag gcgatttctg agccgaagcc ccgcgggacg atttgtgccc      660
cttgctgtgg ctccccaccg cttccccctg gggttggccc tggcagcctt gacccagcag      720
aggcccgccc tgagcggcgt gagcgtggcc tcttccgggt tgctcccgg gcacagcggg      780 ctcagggccc tcgggcatcg ggaggggagc ggtgcgcgtt ggagggtccc gatggggcc      840 ggaatcagct ggggccattc tgggggcgctt tctctcggct ctgggctcgc gactgggaga      900
cctcgggtga ggtctctgtt gccccggagg tgttctgcgt gctgtccgtc tgtgctcagg      960
gctgtgagat gggctcctgg gggccgtcgc gttttctggg aagccccagg ccttttcccg     1020
ctcctgaaga gcctccccga agcgctgtcg ggaagcgctc tcctcaggt cctgcgggtc     1080
```

| | |
|---|---:|
| aggcccggtg tttcggtcca cgagcaccag cttcttccac cgggccgcta agtctctggc | 1140 |
| aaagtcgccc acgtgctggt gcttccgcag gcgcttcacc gtctttctga ttccagtctc | 1200 |
| cgccaggatg tctgcggtca tgggcaaggc ggagagtttc tgcaaatatt tctctagctt | 1260 |
| tttcggctcc gtcttagtgg ccagacgcac ctgcagcttc cccactgcgc gcagcgtagt | 1320 |
| ggaccctgcc gccatctcgc cagagctgtg caggcgtcgc tgtcctcgcg gtcgcggctc | 1380 |
| tgtccgagct cggggcggcg gcacaggcag tctggggtgg ccggtcctcg ctgcccggtc | 1440 |
| gccaggcggc gacctcggga tgtggagtca cagcctggag cgagctgggt cctcggagca | 1500 |
| gcgggccact tggtctggaa cgccggtcct gcagacagc tgagcaggcc cgcttctgtt | 1560 |
| cctcgggatg tgcggccg | 1578 |

<210> SEQ ID NO 25
<211> LENGTH: 584
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is any nucleotide

<400> SEQUENCE: 25

| | |
|---|---:|
| cggccgctgg gtttgttttc acgtgcggat cggattttcg tggtcactac tcgcagncgc | 60 |
| tgctctcggg cgtcccgaag ccgcaggtac agctcccgcc aagactcgtg ctcctgtggc | 120 |
| ttttcttcct tgaagtcctg gaggcaatga atcctccata attcatctgt ctctcgagcg | 180 |
| agtgcggcat tgtctttctc tgtgcggtac ggctgatcgg gcgtccaccc ttccagaacg | 240 |
| ggttcaagaa ccgagtaggg gaccccttcc acgtcgccga gggcgtccgg attgttccta | 300 |
| ggcacccgga ggcactgctg gcgcagcgtc ggcacctgga gctggcaggc aggcctggag | 360 |
| cccgagtaca ccggcatctt agcgttcact ctgcgtccag ggaaagcagc ttcctcctgg | 420 |
| agcgttggcg cggagagtgc ttctgggttt gcctgggagg tcatggcctc aaaagcggac | 480 |
| agcagatcgt agttggcctg catccaggcc tctgaggggt cccagagctc cgagaagaca | 540 |
| tggctgggca ccgttttcgg cccggcggaa tcaagcgccg gccg | 584 |

<210> SEQ ID NO 26
<211> LENGTH: 443
<212> TYPE: DNA
<213> ORGANISM: Homo sapiens
<220> FEATURE:
<221> NAME/KEY: misc_feature
<222> LOCATION: (357)..(434)
<223> OTHER INFORMATION: n is any nucleotide

<400> SEQUENCE: 26

| | |
|---|---:|
| cggccggcaa ggctcaggac ctgcaggcca tggagtggcg aggctgccat ggagtggcga | 60 |
| ggctgccgtg gagcgcggag gccgggtacg cctgcgcgtg gagcgcgaag gccgggtaca | 120 |
| cctgcgcgtg gagcgcggag gccgggtaca cctgcgcgtg gagcgcggag gccgggtaca | 180 |
| cctgcgcgtg gagcgcggag gccgggtaca cctgcgcgtg gagcgcggag gccgggtaca | 240 |
| cctgcgcgtg gagcgcggag gccgggtaca tctgcgcgtg gcacgcggag gccgggtaca | 300 |
| cctgcgctca tcgcacacca gcgcccacgc ccagacgtac tcgcgggaag acagcntttt | 360 |
| tntancnaaa aancgaatgg tcaacccgnt ttanttaaca cgggccancc cggaaacagc | 420 |
| ccgacacgga ccgngacggg ccg | 443 |

<210> SEQ ID NO 27

<211> LENGTH: 157
<212> TYPE: DNA
<213> ORGANISM: Homo sapiens

<400> SEQUENCE: 27

| | | | | | | |
|---|---|---|---|---|---|---|
| cggccgtggc | ttctaccgtg | ctgcggggct | gcgggtcccg | ggtgggccca | ttgcccggtc | 60 |
| acactcggat | cttggaataa | aatgtgggcg | tccatgtgag | gccgaagcag | tggctgtgac | 120 |
| gccccacgcg | gggtgcgatc | tctgcgggag | ccggccg | | | 157 |

<210> SEQ ID NO 28
<211> LENGTH: 689
<212> TYPE: DNA
<213> ORGANISM: Homo sapiens
<220> FEATURE:
<221> NAME/KEY: misc_feature
<222> LOCATION: (457)..(676)
<223> OTHER INFORMATION: n is any nucleotide

<400> SEQUENCE: 28

| | | | | | | |
|---|---|---|---|---|---|---|
| cggccgccat | ctcgccgtcg | tcccgcgggg | tgcccggggc | gttgctcagg | ccggccacgg | 60 |
| cgccggggga | gctcttcggc | aacccgtcca | tgtcgcccga | gcccagggat | ccgcttacgt | 120 |
| ggtgaggctc | catcgcgctc | atggcggcca | tggggccctc | cgggccaggg | ccgagcggga | 180 |
| aattagccct | gccggcaccc | ggcccgatgg | ggttcatgat | agtgtacatg | ttttcactgg | 240 |
| agttggtaga | atctccaggg | ctaggcatga | tgaggtgttc | caggggggccc | acctcctcct | 300 |
| gggggtcccg | tgtagctgcc | aggggatgag | gaggagtagg | ggatcgagtt | tccactgggg | 360 |
| ctggcccacg | ggccacgaac | tcctgggccc | atgttcatgg | caggcaggcc | tgggccggca | 420 |
| agggagttgg | gtgggggtcg | catgccgctc | atagctntgg | ggccccacgc | tggcatgccg | 480 |
| cgaggaggcg | tcaccctncg | cattgggccg | ccatgcttcg | gatgcccctt | gggttcgtgg | 540 |
| ggagggctcc | atggcgccag | ggaggaaggg | atgggaaccc | gggaggcctg | cnggagctga | 600 |
| cttaacatnc | gcagggnggg | nccgggaccc | cctgggaagc | gccgtnacat | taaaggctnn | 660 |
| cccgtgaagg | cccatnacgg | ggcatttgg | | | | 689 |

<210> SEQ ID NO 29
<211> LENGTH: 690
<212> TYPE: DNA
<213> ORGANISM: Homo sapiens
<220> FEATURE:
<221> NAME/KEY: misc_feature
<222> LOCATION: (86)..(682)
<223> OTHER INFORMATION: n is any nucleotide

<400> SEQUENCE: 29

| | | | | | | |
|---|---|---|---|---|---|---|
| cggccgctta | gtcgcagggc | ccgccacccg | agggtcgcgc | agcccactgg | gcccgatgga | 60 |
| gccgccgcgt | gccgggcgcg | tgcgcnanct | cnccegggcg | ggggccgngg | ggcgctaacg | 120 |
| gtcgcaaaca | anttgccgc | cctggccgg | gaggcggctc | aacaccntga | ctgccnacct | 180 |
| acgagacccg | tttacctcan | tgcggngtgt | gctggcggna | nccgcgccg | ctnnaagcaa | 240 |
| taaccgngcc | gccaccgctg | ctgccgcggc | cctgagggag | ccggcccctg | ccctcccgcg | 300 |
| ccccgagtcc | ccactgcnct | ccgnatgtca | anggngcccg | ccccggtncc | gccccatnca | 360 |
| cgttgagacg | cnaacaaaac | ccanacggcc | aggtncaagc | ttnccaagct | ttatttattg | 420 |
| gcaaatttgg | gcggcccnnc | cgcacggcan | ccttcgagnc | anccgccnag | tgtgcaccaa | 480 |
| tcccgcgatg | gngntttaat | cgtgttttt | ctttctgga | tgatataaat | attgaccgna | 540 |
| cacttcntgn | ttgntccagg | gnttttnttt | gggggcccca | aaagccgcat | ttggcctttg | 600 |

```
ggggaanagg ngaaggttcc tgccntnccg nccnanatta naaaaaatng ggantccccc    660
gggccngcag gaattttttnt tncaaactta                                    690

<210> SEQ ID NO 30
<211> LENGTH: 733
<212> TYPE: DNA
<213> ORGANISM: Homo sapiens
<220> FEATURE:
<221> NAME/KEY: misc_feature
<222> LOCATION: (7)..(726)
<223> OTHER INFORMATION: n is any nucleotide

<400> SEQUENCE: 30
cggccgntgt ggccaccacg ctcaatggga actctgtgtt cggaggcgcg ggggccgnct     60
cggctcccac cgggacgccc tcgggacagc cgctggcggt ggcccaagc ctnggctcgt    120 cnccactggt cccggcgccc aacgtgatcc tgcatcgcac acccacgccc attcagccca   180
agcccgcggg ggtgctgccc gcccaanctc taccagctga cgcccaagcc gtttgcgccc   240
gcgggcgcca cgctcaccat ccagggcgag ccggggggcgc tcccgcaagc anccaaggc   300 cccgcanaac ctgacgttca tggcggcggg gaaggcggnc caagaacgtg gtgctgtcgg   360
ggcttccccg cncctgcgct gcaaagcgaa cntntttcaan cagccaccgg gcaccancac   420
cggagcggcc ccgccgcaag ccccgcgggg gcccttgaan anaacccatg atcnttccac   480 cttttcttgaa cccaaggnaa gcagnatttg tcattccccc gcccaannaa catncctgtc   540
cgggccaaaa cncaattttn ctactgntct tgggcacccc cnggcggntg cagctttcct   600
gcagnattct tttaancnct tncccgggnc aacnntgggg ccgggnaana acctnggcgg   660
gcngcttttt aaaantaag tnggattccc ccggggcctg gtaaggaaat nntnaaattn   720
nanagncttt att                                                      733

<210> SEQ ID NO 31
<211> LENGTH: 791
<212> TYPE: DNA
<213> ORGANISM: Homo sapiens

<400> SEQUENCE: 31
cggccgattc ggagagccgg atagggtagg gccgcagaag tttctgagcg cggccaagcc     60 agcagggggcc tcgggcctga gccctcggat cgagatcact ccgtcccacg aactgatcca   120
ggcagtgggg cccctccgca tgagagacgc gggcctcctg gtggagcagc cgcccctggc   180
cggggtggcc gccagcccga ggttcaccct gcccgtgccc ggcttcgagg gctaccgcga   240
gccgctttgc ttgagccccg ctagcagcgg ctcctctgcc agcttcattt ctgacacctt   300 ctcccctac acctcgccct gcgtctcgcc caataacggc gggcccgacg acctgtgtcc   360
gcagtttcaa aacatccctg ctcattattc ccccagaacc tcgccaataa tgtcacctcg   420
aaccagcctc gccgaggaca gctgcctggg ccgccactcg cccgtgcccc gtccggcctc   480
ccgctcctca tcgcctggtg ccaagcggag gcattcgtgc gccgaggcct tggttgccct   540 gccgccccgga gcctcacccc agcgctcccg gagcccctcg ccgcagccct catctcacgt   600
ggcaccccag gaccacggct ccccggctgg gtacccccct gtggctggct ctgccgtgat   660
catggatgcc ctgaacagcc tcgcacgga ctcgccttgt gggatccccc ccaagatgtg   720
gaagaccagc cctgacccct cgccggtgtc tgccgcccca tccaaggccg gcctgcctcg   780
ccacatctac c                                                        791

<210> SEQ ID NO 32
```

```
<211> LENGTH: 20
<212> TYPE: DNA
<213> ORGANISM: Artificial sequence
<220> FEATURE:
<223> OTHER INFORMATION: Amplification primer

<400> SEQUENCE: 32
tctgctgtcc gcttttgagg                                                20

<210> SEQ ID NO 33
<211> LENGTH: 25
<212> TYPE: DNA
<213> ORGANISM: Artificial sequence
<220> FEATURE:
<223> OTHER INFORMATION: Amplification primer

<400> SEQUENCE: 33
atcggatttt cgtggtcact actcg                                          25
```